(12) United States Patent
Markesbery et al.

(10) Patent No.: US 10,603,396 B2
(45) Date of Patent: Mar. 31, 2020

(54) METHODS AND SYSTEM FOR DISINFECTION

(71) Applicants: W. Russell Markesbery, Hebron, KY (US); Eugene J. Pancheri, Cincinnati, OH (US)

(72) Inventors: W. Russell Markesbery, Hebron, KY (US); Eugene J. Pancheri, Cincinnati, OH (US)

(73) Assignee: MARKESBERY BLUE PEARL LLC, Hebron, KY (US)

( * ) Notice: Subject to any disclaimer, the term of this patent is extended or adjusted under 35 U.S.C. 154(b) by 0 days.

(21) Appl. No.: 16/198,570

(22) Filed: Nov. 21, 2018

(65) Prior Publication Data

US 2019/0091360 A1 Mar. 28, 2019

Related U.S. Application Data

(63) Continuation-in-part of application No. PCT/US2017/034519, filed on May 25, 2017.
(Continued)

(51) Int. Cl.
*A61L 9/14* (2006.01)
*A61L 2/22* (2006.01)
(Continued)

(52) U.S. Cl.
CPC .............. *A61L 2/22* (2013.01); *A01N 25/06* (2013.01); *A01N 37/16* (2013.01); *A01N 59/00* (2013.01);
(Continued)

(58) Field of Classification Search
CPC ............... A61L 2/22; A61L 2/186; A61L 9/14
See application file for complete search history.

(56) References Cited

U.S. PATENT DOCUMENTS 5,743,251 A 4/1998 Howell et al.
5,772,971 A 6/1998 Murphy et al.
(Continued)

FOREIGN PATENT DOCUMENTS

CN 104434669 3/2015
CN 105147540 12/2015
(Continued)

OTHER PUBLICATIONS

Bell et al., "Reduction of foodborne micro-organisms on beef carcass tissue using acetic acid, sodium bicarbonate, and hydrogen peroxide spray washes", Oct. 1, 1997, Food Microbiology vol. 14, No. 5, p. 439-448 (10 pages).
(Continued)

*Primary Examiner* — Sean E Conley
(74) *Attorney, Agent, or Firm* — Daniel F. Nesbitt; Daniel H. Lajiness; Hasse & Nesbitt LLC

(57) ABSTRACT

The present disclosure relates to methods and system for disinfecting surfaces within a volumetric space by forming peracids in a reaction layer in situ directly on the surfaces to be disinfected. Particularly, a peroxide compound and an organic acid are sequentially dispersed into the volumetric space, preventing peracids from being formed until the two reactants contact each other on the surface to be disinfected. In some embodiments, any of the dispersed aqueous compositions can optionally be electrostatically charged. Additionally, a system for sequentially dispersing the peracid reactant compounds by electrostatic spraying is provided.

22 Claims, 6 Drawing Sheets

Related U.S. Application Data

(60) Provisional application No. 62/341,799, filed on May 26, 2016.

(51) Int. Cl.
| | |
|---|---|
| *A01N 59/00* | (2006.01) |
| *A01N 25/06* | (2006.01) |
| *A61L 2/18* | (2006.01) |
| *A01N 37/16* | (2006.01) |
| *A61L 2/10* | (2006.01) |
| *B05B 5/053* | (2006.01) |

(52) U.S. Cl.
CPC ............... *A61L 2/183* (2013.01); *A61L 2/186* (2013.01); *A61L 9/14* (2013.01); *A61L 2/10* (2013.01); *A61L 2202/10* (2013.01); *A61L 2202/11* (2013.01); *A61L 2202/15* (2013.01); *A61L 2202/24* (2013.01); *A61L 2202/25* (2013.01); *B05B 5/0535* (2013.01)

(56) References Cited

U.S. PATENT DOCUMENTS

| | | | |
|---|---|---|---|
| 6,234,167 B1 | 5/2001 | Cox et al. | |
| 6,491,233 B2 | 12/2002 | Nichols | |
| 6,501,052 B2 | 12/2002 | Cox et al. | |
| 6,516,796 B1 | 2/2003 | Cox et al. | |
| 6,557,552 B1 | 5/2003 | Cox et al. | |
| 6,568,390 B2 | 5/2003 | Nichols et al. | |
| 6,640,050 B2 | 10/2003 | Nichols et al. | |
| 6,681,769 B2 | 1/2004 | Sprinkel, Jr. et al. | |
| 6,681,998 B2 | 1/2004 | Sharpe et al. | |
| 6,692,694 B1 | 2/2004 | Curry et al. | |
| 6,701,921 B2 | 3/2004 | Sprinkel, Jr. et al. | |
| 6,715,487 B2 | 4/2004 | Nichols et al. | |
| 6,766,220 B2 | 7/2004 | McRae et al. | |
| 6,772,757 B2 | 8/2004 | Sprinkel, Jr. et al. | |
| 6,799,572 B2 | 10/2004 | Nichols et al. | |
| 6,804,458 B2 | 10/2004 | Sherwood et al. | |
| 6,883,516 B2 | 4/2005 | Hindle et al. | |
| 6,923,179 B2 | 8/2005 | Gupta et al. | |
| 7,040,314 B2 | 5/2006 | Nguyen et al. | |
| 7,077,130 B2 | 7/2006 | Nichols et al. | |
| 7,117,867 B2 | 10/2006 | Cox et al. | |
| 7,128,067 B2 | 10/2006 | Byron et al. | |
| 7,147,170 B2 | 12/2006 | Nguyen et al. | |
| 7,159,507 B2 | 1/2007 | Grollimund et al. | |
| 7,163,014 B2 | 1/2007 | Nichols et al. | |
| 7,167,776 B2 | 1/2007 | Maharajh et al. | |
| 7,173,222 B2 | 2/2007 | Cox et al. | |
| 7,351,684 B2 | 4/2008 | Tichy et al. | |
| 7,367,334 B2 | 5/2008 | Faison, Jr. et al. | |
| 7,373,938 B2 | 5/2008 | Nichols et al. | |
| 7,400,940 B2 | 7/2008 | McRae et al. | |
| 7,473,675 B2 | 1/2009 | Tichy et al. | |
| 7,500,479 B2 | 3/2009 | Nichols et al. | |
| 7,534,756 B2 | 5/2009 | Tichy et al. | |
| 7,743,766 B2 | 6/2010 | Gupta et al. | |
| 8,034,759 B2 | 10/2011 | Man et al. | |
| 8,110,538 B2 | 2/2012 | Martin et al. | |
| 8,442,390 B2 | 5/2013 | Nichols et al. | |
| 8,696,986 B2 | 4/2014 | Rovison, Jr. et al. | |
| 8,716,339 B2 | 5/2014 | Larson et al. | |
| 8,746,597 B2 | 6/2014 | Sides | |
| 8,772,218 B2 | 7/2014 | Cunningham et al. | |
| 8,789,716 B2 | 7/2014 | Larson et al. | |
| 8,987,331 B2 | 3/2015 | Larson et al. | |
| 9,044,403 B2 | 6/2015 | Shultz | |
| 9,050,384 B2 | 6/2015 | Grant et al. | |
| 9,061,300 B2 | 6/2015 | Belcastro et al. | |
| 9,192,909 B2 | 11/2015 | Kraus et al. | |
| 9,241,483 B2 | 1/2016 | Golden et al. | |
| 2004/0120844 A1 | 6/2004 | Tribelsky et al. | |
| 2005/0238631 A1 | 10/2005 | Burwell | |
| 2006/0289354 A1 | 12/2006 | Zhou et al. | |
| 2007/0231200 A1 | 10/2007 | Lin et al. | |
| 2007/0262478 A1 | 11/2007 | Price et al. | |
| 2008/0000931 A1 | 1/2008 | Tichy et al. | |
| 2008/0241269 A1 | 10/2008 | Velasquez | |
| 2009/0246336 A1 | 10/2009 | Burnett et al. | |
| 2010/0316530 A1 | 12/2010 | Morgantini et al. | |
| 2013/0199539 A1 | 8/2013 | Webster | |
| 2013/0316055 A1 | 11/2013 | Holt | |
| 2013/0326055 A1 | 11/2013 | Holt | |
| 2014/0178249 A1 | 6/2014 | Tichy et al. | |
| 2014/0238445 A1 | 8/2014 | Stokes et al. | |
| 2014/0275267 A1 | 9/2014 | Beug-Deeb et al. | |
| 2014/0328949 A1 | 11/2014 | Adams et al. | |
| 2014/0378544 A1 | 12/2014 | Kraus et al. | |
| 2015/0102061 A1 | 4/2015 | Larson et al. | |
| 2015/0297770 A1 | 10/2015 | Larson et al. | |
| 2016/0022850 A1 | 1/2016 | Tsai et al. | |

FOREIGN PATENT DOCUMENTS

| | | |
|---|---|---|
| CN | 106509445 | 3/2017 |
| EP | 0411970 | 2/1991 |
| GB | 2257630 | 1/1993 |
| GB | 2469018 | 10/2010 |
| WO | 9746626 | 12/1997 |
| WO | 0128511 | 4/2001 |
| WO | 0134211 | 5/2001 |
| WO | 2010056871 | 5/2010 |
| WO | 2011044916 | 4/2011 |
| WO | 2011139300 | 11/2011 |
| WO | 2015074144 | 5/2015 |
| WO | 2017205649 | 11/2017 |

OTHER PUBLICATIONS

Hillsboro, Sanitizing with Vinegar and Hydrogen Peroxide, Mar. 29, 2012, The Urban Homestead, https://www.thriftyfun.com/tf23602306.tip.html (5 pages).
Sumner, "Peroxide and Vinegar Sterilization", Apr. 11, 2011, Cook's Info, http://web.archive.org/web/20160713134637/http://www.cooksinfo.com/peroxide-vinegar-sterilization (3 pages).
International Search Report and Written Opinion dated May 7, 2019 for related International Application No. PCT/US2018/055367 filed Oct. 11, 2018 (20 pages).
Multi-Clean, "Targeting Pathogens: Electrostatic Spraying of Disinfectant Solutions", May 26, 2016, https://multi-clean.com/targeting-pathogens-electrostatic-spraying-disinfectant-solutions/ (6 pages).
Non-final Office Action dated Jun. 17, 2019 in related U.S. Appl. No. 16/202,269, filed Nov. 28, 2018 (16 pages).
Extended European Search Report and Opinion dated May 2, 2019 in related European Application No. 18208959.9 filed Nov. 28, 2018 (7 pages).
"Acute Exposure Guideline Levels for Selected Airborne Chemicals", Committee on Acute Exposure Guideline Levels; Committee on Toxicology, & Board on Environmental Studies and Toxicology, National Research Council of the National Academies, The National Academies Press, Washington, D.C., vol. 8, Chapter 7, 2010, pp. 327-367 (41 pages).
"Common Chemicals Used for Cleaning and Decontamination Guideline", Department of Environmental Health and Safety, University of Colorado, Aug. 2014, (3 pages).
International Search Report and the Written Opinion of the International Searching Authority, dated Jul. 24, 2017, for corresponding application No. PCT/US2017/034519, Filed May 25, 2017 (15 pages).
Nyamunda, B. C., et al., "Hydrogen Peroxide as an Oxidant for Organic Reactions", Journal of Atoms and Molecules, vol. 3, No. 1, Feb. 2013 (23 pages).
Pavliv, L, et al., "Formulation and Manufacturing", Drug and Biological Development : From Molecule to Product and Beyond, Ronald Evens, editor, Springer US, publisher, p. 210, 2007 (1 page).
Rutala, William, et al., "Guideline for Disinfection and Sterilization in Healthcare Facilities, 2008", Center for Disease Control, Dept. of Health and Human Services, USA, pp. 7-30 and 50-51, 2008, (158 pages).

(56) References Cited

OTHER PUBLICATIONS

Zhao, Xuebing, et al., "Preparation of Peracetic Acid from Acetic Acid and Hydrogen Peroxide : Experimentation and Modeling, The Chinese Journal of Process Engineering", vol. 8, No. 1, Feb. 2008 (7 pages).

Zhao, Xuebing, et al., "Preparation of Peracetic Acid from Hydrogen Peroxide Part I : Kinetics for Peracetic Acid Synthesis and Hydrolysis", Journal of Molecular Catalysis A : Chemical, vol. 271, Mar. 12, 2007 (7 pages).

First Office Action dated Dec. 31, 2019 in U.S. Appl. No. 16/202,269, filed Nov. 28, 2018 (19 pages).

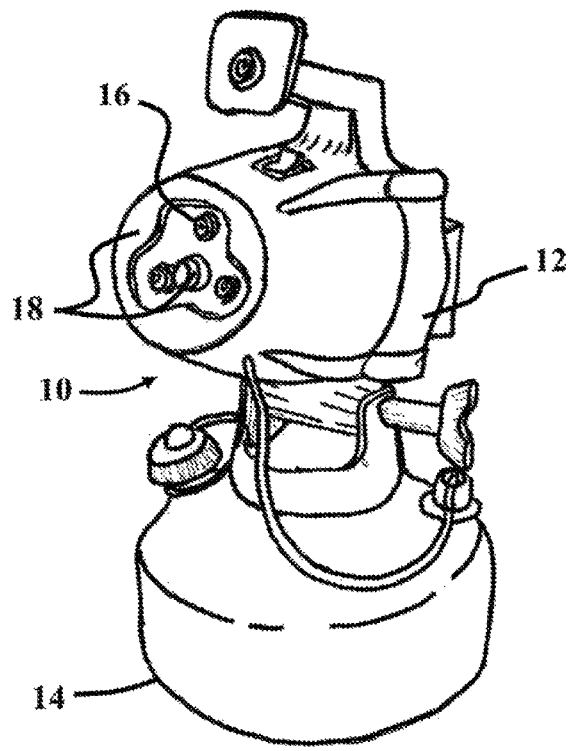
Figure 1 – Prior Art
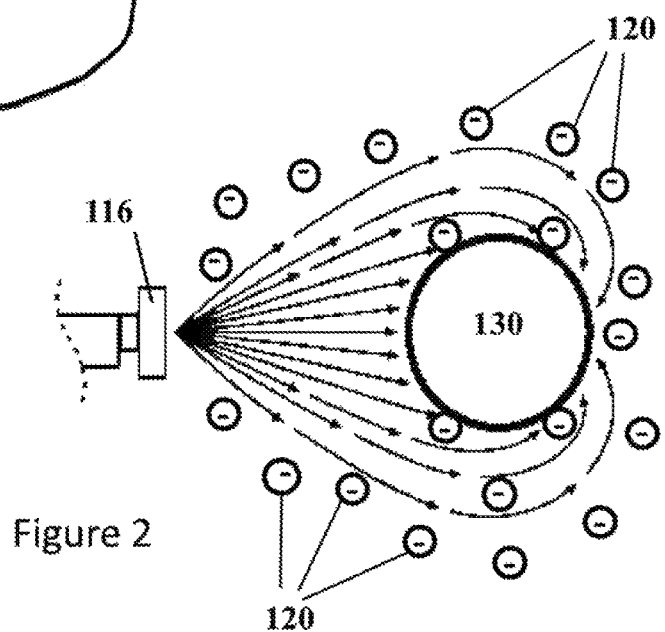
Figure 2

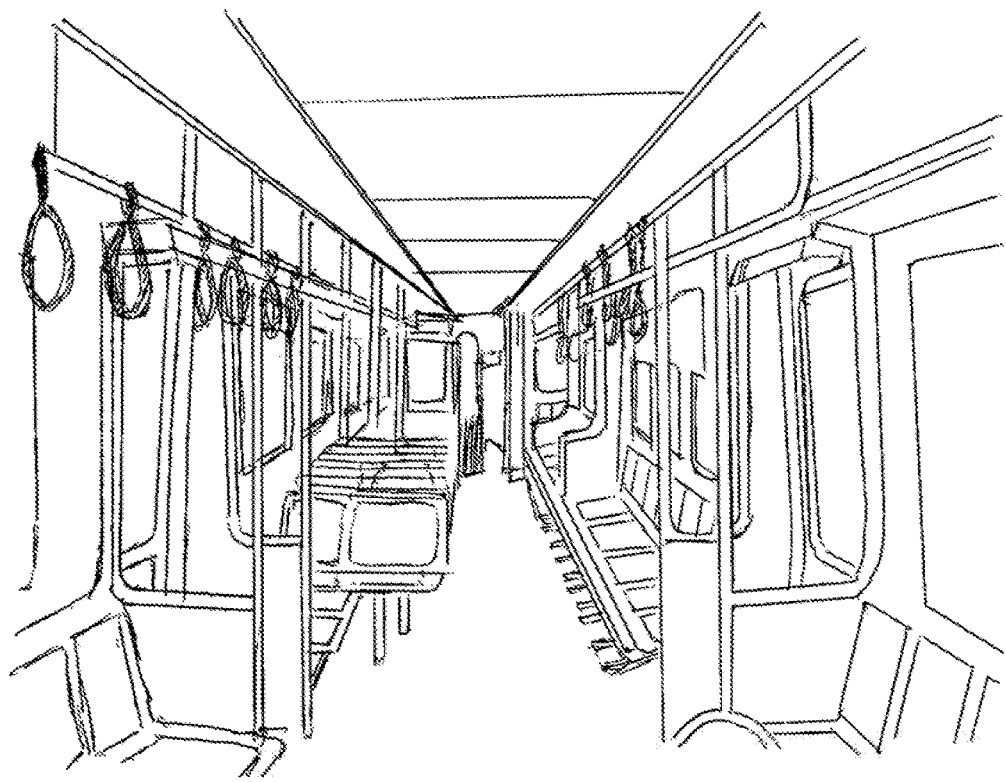
Figure 3 – Prior Art
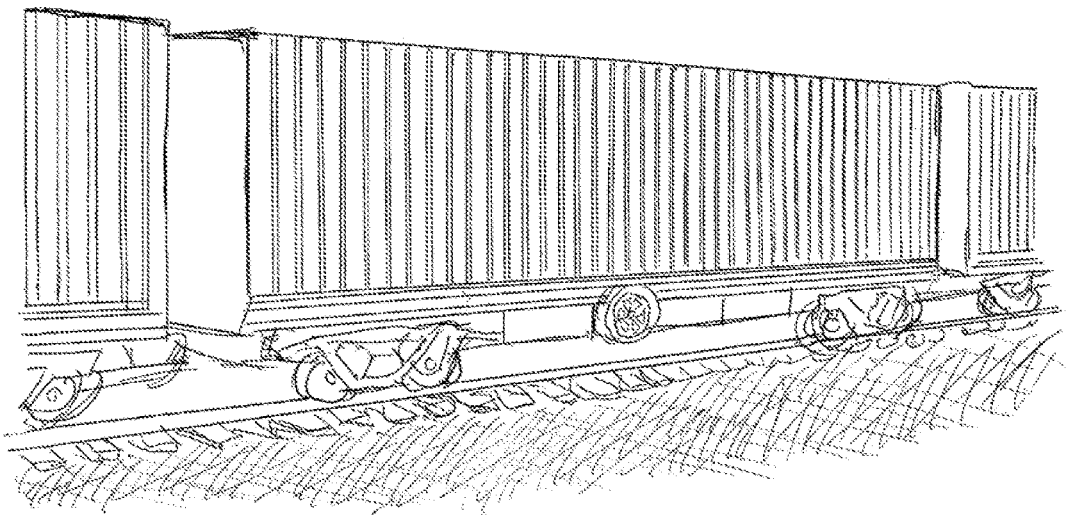
Figure 4 – Prior Art

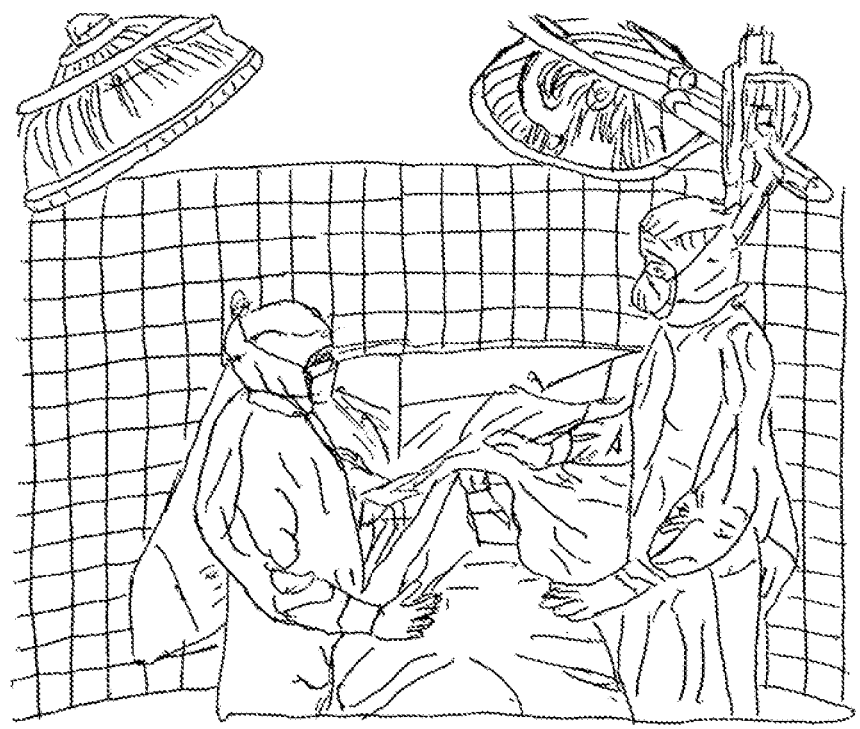
Figure 5 – Prior Art
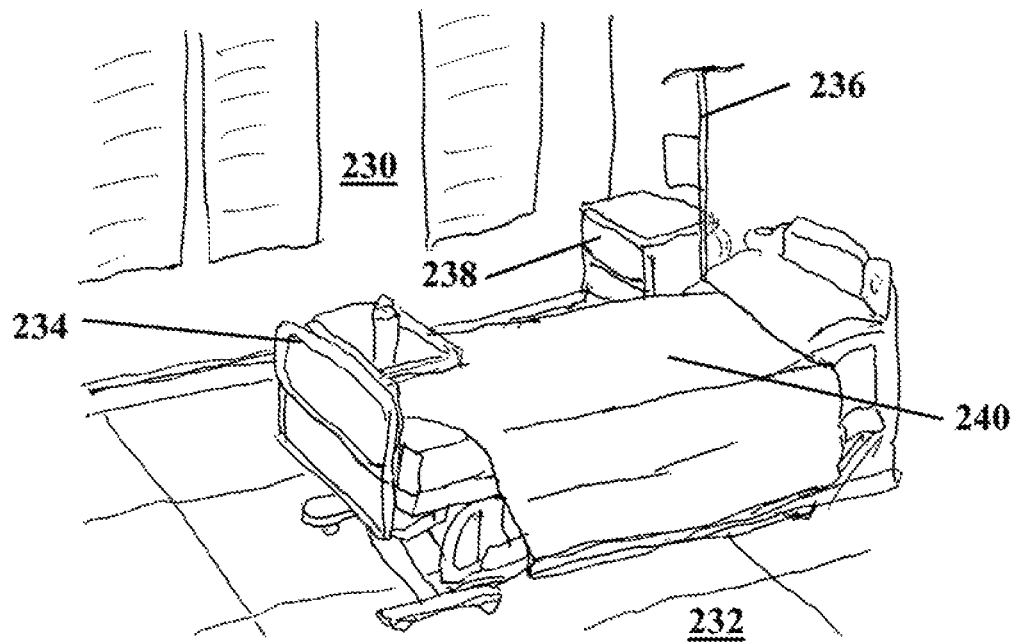
Figure 6 – Prior Art

METHODS AND SYSTEM FOR DISINFECTION

CROSS-REFERENCE TO RELATED APPLICATIONS

The present invention is a continuation-in-part of PCT Application No. PCT/US2017/034519, filed May 25, 2017, which claims the benefit of U.S. Provisional Application No. 62/341,799, filed May 26, 2016, the disclosures of which are incorporated herein by reference in their entireties.

FIELD OF THE INVENTION

The present invention is in the field of disinfection and sterilization methods.

BACKGROUND OF THE INVENTION

There is a need for an inexpensive, effective, yet safe and convenient method to minimize the microbial burden of objects we interact with. In addition, this method must not leave behind microbes with resistance to future treatment. This need is primarily evidenced by unacceptably high rates of infection in hospitals and health care facilities. But there are also problems in daycare facilities, schools, the food industry and the travel industry, among others. Additionally, these problems are becoming more severe as microbes which are resistant to virtually all known antibiotics are becoming more common. It has been predicted that we may soon enter a post-antibiotic era that will be similar to the pre-antibiotic era in which even minor infections will be life threatening.

Consequently, a method for killing virtually all microbes is needed that prevents the microbes from developing a resistance and with ingredient compounds that are not hazardous to humans, pets and other beneficial life that may be exposed to them. A potential way to do this would be to utilize ingredients and methods that are relatively safe to humans but are biocidal.

For centuries prior to the antibiotic era, humans had safely utilized natural biocides. Vinegar has been well known to protect foodstuffs from the effect of microbes, evidenced by many foods being pickled. Ethanol (drinking alcohol) has also been used for years. In Europe, for example, medieval monks who brewed and drank wine or beer instead of the local water had much longer life spans. Additionally, certain spices, essential oils, and honey also have antimicrobial properties. More recently, hydrogen peroxide has been shown to fight microbes, and has long been an internal method that evolved in the animals' eternal fight against the microbes that infest them. Electricity has a biocidal effect. Also, sunlight emits energy in the ultraviolet wavelengths, what is well-known for its biocidal properties.

The problem with these safe biocides is that each one individually is not effective against all types of microbes, and several target microbes have developed defense mechanisms against these biocides. However, combinations of two or more of these biocides have proven to work synergistically to enhance each one's effects. Particularly, combining hydrogen peroxide and acetic acid (the primary component of vinegar) to form peroxyacetic acid has proven to be especially effective. Several methods, apparatuses, and disinfecting systems utilizing peracids, including peroxyacetic acid, have been described in U.S. Pat. Nos. 6,692,694, 7,351,684, 7,473,675, 7,534,756, 8,110,538, 8,696,986, 8,716,339, 8,987,331, 9,044,403, 9,050,384, 9,192,909, 9,241,483, and U.S. Patent Publications 2015/0297770 and 2014/0178249, the disclosures of which are incorporated by reference in their entireties.

However, one of the biggest drawbacks with using peracids is that they are easily hydrolyzed to produce ordinary acids and either oxygen or water. Consequently, peroxyacetic acid has limited storage stability and a short shelf life. Peroxyacetic acid instability is described in detail in U.S. Pat. No. 8,034,759, the disclosure of which is incorporated by reference in its entirety. Often, commercially available products contain additional components to combat this problem, by including either a large excess of hydrogen peroxide to drive equilibrium toward the peracid form, or stabilizers such as other acids, oxidizing agents, and surfactants. Some methods have prevented degradation during shipping and storage by requiring that individual components of a peracid composition be mixed together, and subsequently applied, at the location and time that a target will be disinfected or sterilized. Yet these methods nonetheless require expensive additives that are difficult to obtain, such as polyhydric alcohols, esters, and transition metals, as well as specific reaction conditions.

As a non-limiting example of the measures taken to stabilize peracid compositions, U.S. Pat. No. 8,716,339 describes a disinfectant system that includes a first chamber containing a first solution that includes an alcohol, an organic carboxylic acid, and a transition metal or metal alloy, and a second chamber containing a second solution that includes hydrogen peroxide. Prior to disinfecting, the system is configured to mix the first and second solutions prior to dispensing the mixture onto a surface. Mixing the first and second solutions forms a peracid within the disinfectant system prior to dispensing, but the presence of the transition metal is required to help stabilize the peracid in the period between when the solutions are mixed and when the mixture reaches the contaminated surface.

Similarly, U.S. Pat. No. 8,110,538 describes microbicidal, antimicrobial, and decontaminant compositions containing peroxides and peracids with equilibrium reaction products in combination with photoreactive surfactants and polymers, wherein the polymer interacts with the peracids and peroxides. Such equilibrium reaction products include organic acids such as acetic acid and other carboxylic acids. By including an excess amount of hydrogen peroxide and an organic acid, the composition leverages Le Chatelier's principle to drive equilibrium away from peracid hydrolysis, stabilizing the presence of the peracid within the composition. Furthermore, the polymer further acts as a stabilizer by forming adducts and chemical complexes with the peracids and peroxides within the composition.

In both of the above examples, the additionally-added components serve to stabilize the peracid compositions prior to dispensing them onto a surface to be disinfected. However, these components are expensive, relatively scarce, and can have undesirable effects within the environment to be disinfected. Such undesirable effects often include the leaving of residues, films, stains, and pungent odors on treated surfaces and surface areas that require time, money, and effort to remove, if they can be removed at all. Even if those undesirable effects can be later remedied, there are known safety concerns associated with dispersing airborne particles or peracids into the environment in an effort to sterilize that environment. Safety data and recommended exposure levels are described in detail in Acute Exposure Guideline Levels for Selected Airborne Chemicals, National Research Council (US) Committee on Acute Exposure Guideline Levels, pg. 327-367, Volume 8, 2010, the disclosure of which is hereby incorporated by reference in its entirety.

As a result, there is still a need for sterilization and disinfecting methods utilizing peracids that are simultaneously effective, convenient, and safe, while at the same time using cheap and readily available materials.

SUMMARY OF THE INVENTION

The present invention provides a method for disinfecting surfaces using peracid chemistry while eliminating instability issues and human safety issues associated with forming the peracid at any point prior to contacting a surface. The present invention provides improved methods for disinfecting surfaces by dispersing peracid reactant compounds in separate application steps and forming in situ the peracid directly on the surface.

In some embodiments, a broad and complete microbe kill is achieved through careful selection of substantially different mechanisms acting in concert with each other, in order that no microbe can develop mutations that would render future generations resistant. In further embodiments, the methods described herein can provide a prophylactic coating that can protect certain surfaces from corrosion and/or microbial contamination.

The present invention provides a method of disinfecting a surface in need of disinfecting within a volumetric space, comprising the steps of: a) dispersing into the volumetric space a multiplicity of droplets of a first aqueous composition comprising a first peracid reactant compound that is either a peroxide compound or an organic acid, wherein the multiplicity of droplets of the first aqueous composition deposits onto the surface; and b) dispersing into the volumetric space a multiplicity of droplets of a second aqueous composition comprising a second peracid reactant compound that is the other of the first peracid reactant compound, wherein the multiplicity of droplets of the second aqueous composition deposits upon the surface and coalesces with the multiplicity of droplets of the first aqueous composition, thereby forming one or more composition pools upon the surface, and forming the peracid in situ within each composition pool, and disinfecting the surface.

In one embodiment, the multiplicity of droplets of the first aqueous composition deposited onto the surface coalesces into one or more first aqueous composition pools upon at least a portion of the surface, and alternatively, into a first aqueous composition layer upon the surface.

In another embodiment, a method of disinfecting a surface in need of disinfecting within a volumetric space comprises the steps of: a) dispersing into the volumetric space a multiplicity of droplets of a first aqueous composition comprising a first peracid reactant compound that is either a peroxide compound or an organic acid, wherein the multiplicity of droplets of the first aqueous composition deposits and coalesces into a first aqueous composition layer upon the surface; and b) dispersing into the volumetric space a multiplicity of droplets of a second aqueous composition comprising a second peracid reactant compound that is the other of the first peracid reactant compound, wherein the multiplicity of droplets of the second aqueous composition deposits onto the coalesced first aqueous composition layer to form a reaction layer upon the surface, thereby forming a peracid in situ within the reaction layer and disinfecting the surface.

In another embodiment, a method of disinfecting a surface in need of disinfecting within a volumetric space comprises the steps of: a) dispersing into the volumetric space a multiplicity of droplets of a first aqueous composition comprising a first peracid reactant compound that is either a peroxide compound or an organic acid compound capable of reacting with a peroxide compound to form a peracid; b) allowing a time sufficient for the multiplicity of droplets of the first aqueous composition to distribute throughout the volumetric space, and to deposit and coalesce into a layer upon the surface; c) dispersing into the volumetric space a multiplicity of droplets of a second aqueous composition comprising a second peracid reactant compound that is the other of the first peracid reactant compound; and d) allowing a second time sufficient for the multiplicity of droplets of the second aqueous composition to deposit onto the coalesced layer of the first aqueous composition to form a reaction layer, thereby forming a peracid in situ on the reaction layer and disinfecting the surface.

In another embodiment, the pH of the aqueous composition comprising the organic acid is less than or equal to about 7. In further embodiments, the pH of the reaction layer is less than or equal to about 7.

In another embodiment, the stoichiometric amount of the dispersed peroxide compound is equal to or greater than the stoichiometric amount of the dispersed organic acid. In further embodiments, the stoichiometric amount of the peroxide compound in the reaction layer is equal to or greater than the stoichiometric amount of the organic acid in the reaction layer.

In another embodiment, one or more of the aqueous compositions have a volatility such that at least 90% of the reaction layer can evaporate within 30 minutes of being formed. In further embodiments, at least 95% of the reaction layer can evaporate, at standard conditions, within 30 minutes of being formed. In even further embodiments, at least 99% of the reaction layer can evaporate within 30 minutes of being formed. In still further embodiments, at least 99.5% of the reaction layer can evaporate within 30 minutes of being formed. In yet further embodiments, at least 99.7% of the reaction layer can evaporate within 30 minutes of being formed. In still yet further embodiments, at least 99.9% of the reaction layer can evaporate within 30 minutes of being formed.

In another embodiment, the individual components of one or more of the aqueous compositions can be selected to have vapor pressures that facilitate the evaporation of the reaction layer after sterilization of the surfaces within the volumetric space is complete. In further embodiments, one or both of the aqueous compositions can be formulated so at least about 99.0, 99.5, or 99.9% of the components by weight of the aqueous composition have a vapor pressure of at least 1.0 mm Hg at 20° C. In even further embodiments, one or both of the aqueous compositions can be formulated so that essentially 100% of the components by weight of the aqueous composition have a vapor pressure of at least about 1.0 mm Hg at 20° C.

In another embodiment, the effective diameter of the multiplicity of droplets is controlled to be small enough to allow the droplets to reach a diversity of the intended surfaces to be disinfected within a volumetric space, and to be large enough to minimize deep lung penetration if the droplets were to be inhaled. In further embodiments, a preponderance of the multiplicity of droplets dispersed into the volumetric space has an effective diameter of at least about 1 micron, including at least about 5, 10, 15, 20, 25, 30, 35, 40, 45, 50, 60, 70, 80, or 90 microns, up to about 100 microns. In even further embodiments, the preponderance of the multiplicity of droplets dispersed into the volumetric space has an effective diameter of about 10 microns to about 25 microns. In still further embodiments, the preponderance of the multiplicity of droplets dispersed into the volumetric space has an effective diameter of about 15 microns.

In another embodiment, the time sufficient for the multiplicity of droplets to distribute throughout the volumetric space and to deposit onto a surface is the time for a coalesced layer to be formed on substantially all of the intended surfaces to be disinfected within a volumetric space, based on factors including, but not limited to, the desired droplet size, the atmospheric conditions within and the volume of the volumetric space, and properties of the aqueous compositions themselves. In other embodiments, the time sufficient for the multiplicity of droplets to distribute throughout the volumetric space and to deposit onto a surface can be used to define a specific amount of time that elapses between the sequential dispersion of successive aqueous compositions. In further embodiments, the time sufficient to allow the aqueous composition to distribute throughout the volumetric space and deposit onto the surfaces to be disinfected is at least about 1 minute, including at least about 5 minutes, or at least about 10 minutes, or at least about 20 minutes, or at least about 30 minutes, and up to at least about 60 minutes, including up to about 30 minutes, or up to about 20 minutes, or up to about 15 minutes.

In another embodiment, a time sufficient for droplets to distribute throughout the volumetric space and deposit on the surfaces to be disinfected can be utilized for one or more of the dispersed aqueous compositions. In some embodiments, the method further comprises the step of allowing a first time sufficient for the multiplicity of droplets of the first aqueous composition to distribute throughout the volumetric space prior to depositing and coalescing into a layer upon the surface. In other embodiments, the method further comprises the step of allowing a second time sufficient for the multiplicity of droplets of the second aqueous composition to distribute throughout the volumetric space prior to depositing onto the coalesced first aqueous composition layer and forming a reaction layer upon the surface. In still other embodiments, a step allowing a time sufficient for droplets of the first aqueous composition to distribute and deposit onto the surface to form a coalesced first aqueous composition layer and a step allowing a time sufficient for droplets of the second aqueous composition to distribute throughout the volumetric space and deposit onto the coalesced first aqueous composition layer to form a reaction layer can be included in the same disinfection method, as described above.

In another embodiment, the method can further comprise the step of allowing a third time sufficient when dispersing droplets of a third aqueous composition consisting essentially of water into the volumetric space, in order for droplets of the third aqueous composition to distribute throughout the volumetric space and/or deposit onto the surfaces to be disinfected, as described below.

In another embodiment, the coalesced layer of the first and second aqueous compositions have, respectively, an effective uniform thickness. In further embodiments, the coalesced layer has an effective uniform thickness of at least about 1 micron, including at least about 2, or 3, or 5, or 8, or 10, or 15, microns, up to about 20 microns. In even further embodiments, the coalesced layer has an effective uniform thickness of about 3 microns to about 8 microns.

In another embodiment, the peroxide compound can include such non-limiting peroxides as hydrogen peroxide, metal peroxides, and ozone. In further embodiments, the aqueous composition comprising the peroxide compound comprises at least about 0.1% by weight of the peroxide compound, including at least about 0.5, 1, 2, 4, 6, 8, 10, 12, 14, 16, 18, or 20% by weight, up to about 25% by weight. In even further embodiments, the aqueous composition comprising the peroxide compound comprises about 5% to about 15% by weight of the peroxide compound. In still further embodiments, the aqueous composition comprising the peroxide compound comprises about 10% of the peroxide compound. In yet further embodiments, the peroxide compound is hydrogen peroxide. In still yet further embodiments, hydrogen peroxide is dispersed within the first aqueous composition.

In another embodiment, the organic acid can be any organic acid capable of forming a peracid upon reacting with a peroxide compound. In further embodiments, the aqueous composition comprising the organic acid comprises at least about 0.5% by weight of the organic acid, including at least about 1, 2, 5, 10, 15, 20, 25, 30, 35, 40, or 45% by weight, up to about 50% by weight. In even further embodiments, the aqueous composition comprising the organic acid comprises about 2% to about 20% by weight of the organic acid. In still further embodiments, the aqueous composition comprising the organic acid comprises about 10% by weight of the organic acid. In yet further embodiments, the organic acid is dispersed within the second aqueous composition.

In another embodiment, the organic acid has one or more carboxylic acid functional groups. In further embodiments, the organic carboxylic acid is selected from the group consisting of: formic acid, acetic acid, citric acid, succinic acid, oxalic acid, propanoic acid, lactic acid, butanoic acid, pentanoic acid, and octanoic acid. In even further embodiments, the organic acid is acetic acid.

In another embodiment, at least one of the first aqueous composition or the second aqueous composition further comprises one or more alcohols. In further embodiments, the aqueous composition comprises at least about 0.05% by weight of the one or more alcohols, including at least about 0.1, 1, 5, 10, 15, 20, 25, 30, 40, 50, or 60% by weight, up to about 70% by weight. In even further embodiments, the aqueous composition comprises about 1% to about 25% by weight of the one or more alcohols. In still further embodiments, the aqueous composition comprises about 15% by weight of the one or more alcohols. In yet further embodiments, each of the one or more alcohols comprises at least 1 carbon atom, up to 24 carbon atoms. In yet still further embodiments, the one or more alcohols includes a lower-chain alcohol selected from the group consisting of ethanol, isopropanol, and t-butanol, and mixtures thereof. In even yet still further embodiments, the one or more alcohols comprises isopropanol.

In another embodiment, aqueous compositions comprising one or more alcohols comprise a reduced surface tension with respect to pure water. In further embodiments, aqueous compositions comprising one or more alcohols have a surface tension less than 72 dyne/cm at 20° C. In even further embodiments, aqueous compositions comprising one or more alcohols has a surface tension less than 30 dyne/cm at 20° C.

In another embodiment, at least one of the first aqueous composition or the second aqueous composition further comprises one or more natural biocides. As a non-limiting example, such compounds include manuka honey and/or essential oils. In further embodiments, the essential oils are selected from the essential oils of oregano, thyme, lemongrass, lemons, oranges, anise, cloves, aniseed, cinnamon, geraniums, roses, mint, peppermint, lavender, citronella, eucalyptus, sandalwood, cedar, rosmarin, pine, vervain fleagrass, and ratanhiae, including combinations thereof. In even further embodiments, the aqueous composition comprises about 0.001% to about 1% by weight of the natural biocide.

In other embodiments, at least one of the first aqueous composition or the second aqueous composition further comprises one or more natural biocidal compounds commonly found within manuka honey and essential oils. In further embodiments, the natural biocidal compounds are selected from the group consisting of methylglyoxal, carvacrol, eugenol, linalool, thymol, p-cymene, myrcene, borneol, camphor, caryophillin, cinnamaldehyde, geraniol, nerol, citronellol, and menthol, including combinations thereof. In even further embodiments, the aqueous composition comprises about 0.001% to about 1% by weight of the natural biocidal compound.

In another embodiment, the method further includes the step of illuminating at least one of the first aqueous composition, the second aqueous composition, and the reaction layer with a wavelength consisting essentially of ultraviolet light.

In another embodiment, the multiplicity of droplets of the first aqueous composition and/or the second aqueous composition are electrostatically charged.

In another embodiment, the multiplicity of droplets of the first aqueous composition and/or the multiplicity of droplets of the second aqueous composition are electrostatically charged. In further embodiments, the multiplicity of droplets of the second aqueous composition are electrostatically charged with the opposite polarity of the multiplicity of droplets of the first aqueous composition.

In another embodiment, the electrostatic charge of the multiplicity of droplets of the first aqueous composition and the second aqueous composition are optimized to provide the most desirable reaction of the first and second peracid reactant compounds. In further embodiments, the multiplicity of droplets of the aqueous composition comprising the peroxide compound are dispersed with a negative charge. In other embodiments, the multiplicity of droplets of the aqueous composition comprising the organic acid are dispersed with a positive charge.

In another embodiment, the surface in need of disinfecting is grounded.

In another embodiment, the multiplicity of droplets of the first aqueous composition and the second aqueous composition are formed by heating the first aqueous composition and the second aqueous composition to produce a vapor phase comprising the respective peracid reactant compound in the ambient air, which distributes throughout the volumetric space, cools and condenses into liquid droplets, and deposits onto the surfaces to be disinfected.

In another embodiment, the multiplicity of droplets of the first aqueous composition and the second aqueous composition are formed by heating the first aqueous composition and the second aqueous composition to produce a vapor phase comprising the respective peracid reactant compound in the ambient air, and allowing a time sufficient for the vapor phase comprising the peracid reactant compound to distribute throughout the volumetric space, to cool and condense into liquid droplets, and to deposit onto the surfaces to be disinfected. In further embodiments, the time sufficient for an aqueous composition dispersed as a vapor to distribute throughout the volumetric space, to cool and condense into liquid droplets, and to deposit onto the surfaces to be disinfected is at least about 10 minutes, including at least about 20 minutes, 30 minutes, 40 minutes, 50 minutes, 1 hour, or 2 hours, up to at least about 3 hours. In even further embodiments, lingering or excess vapor or droplets within the volumetric space can be exchanged using an air exchanger to facilitate the dispersion of a subsequent aqueous composition and/or to return the air within the volumetric space to habitable conditions.

In another embodiment, the first aqueous composition and the second aqueous composition are heated, separately, to a temperature of greater than about 250° C. Alternatively, the first aqueous composition and the second composition are heated, separately, to a temperature sufficient to vaporize the mass of the first aqueous composition and the second aqueous composition in a vaporizing time of less than about 30 minutes, including less than about 25, less than about 20, less than about 15, less than about 10, or less than about 5, minutes. In a further embodiment, the first aqueous composition and the second composition are heated, separately, to a temperature sufficient to vaporize the mass of the first aqueous composition and the second aqueous composition in about two minutes.

In another embodiment, the first aqueous composition and the second aqueous composition in the vapor phase are, separately, cooled to a temperature of less than about 55° C. to condense into droplets and deposit onto surfaces within the volumetric space to be disinfected.

In another embodiment, the first aqueous composition in the vapor phase is formed by introducing the first aqueous composition into a first hot gaseous stream, and the second aqueous composition in the vapor phase is formed by introducing the second aqueous composition into a second hot gaseous stream.

In another embodiment, one or more aqueous compositions are comprised of food-grade components. In further embodiments, one or more aqueous compositions are substantially free of surfactants, polymers, chelators, and metal colloids or nanoparticles.

In another embodiment, the application of the first aqueous composition and the second aqueous composition achieve a log-6 or greater kill of microbes.

In another embodiment, the method further includes the steps of dispersing into the volumetric space a multiplicity of droplets of a third aqueous composition. In even further embodiments, the multiplicity of droplets of the third aqueous composition are electrostatically charged.

In another embodiment, the method can further include the step of dispersing into the volumetric space a pre-treating composition consisting essentially of water, in order to increase the humidity in the volumetric space to stabilize or maintain dispersed droplets of aqueous compositions containing peracid reactant compounds, and to limit or prevent the droplets of the aqueous compositions from being lost or evaporated into the environment or the volumetric space before they deposit onto the surface to be disinfected. In some embodiments, sufficient volume or mass of a pre-treatment composition consisting essentially of water can be dispersed into the volumetric space in order to raise the relative humidity in the volumetric space to at least one of about 50, including at least about 60, least about 70, least about 80, least about 90, least about 95 or least about 99, percent. In further embodiments, sufficient volume or mass of a pre-treatment composition consisting essentially of water can be dispersed into the volumetric space in order to raise the relative humidity in the volumetric space to at least one of about 80, including least about 90, least about 95 or least about 99, percent.

In another embodiment, the method can include a step of dispersing into the volumetric space an intermediate composition consisting essentially of water, after the dispersion of the first aqueous composition comprising the first peracid reactant compound, in order to coalesce with and enhance deposition of any excess or lingering droplets of the first aqueous composition from the air.

In another embodiment, the method can include a step of dispersing into the volumetric space a finishing composition consisting essentially of water, after the dispersion of the second aqueous composition comprising the second peracid reactant compound to coalesce with and enhance deposition of any excess or lingering droplets of the second aqueous composition.

In another embodiment, the effective diameter of a preponderance of the droplets of an aqueous composition consisting essentially of water is at least about 1, including at least at 10, at least about 20, at least about 30, at least about 40, at least about 50, or at least about 100 microns. Preferably, the effective diameter of a preponderance of droplets of the third aqueous composition is about 20 microns to about 30 microns. In other embodiments, the preponderance of the multiplicity of droplets have an effective diameter of less than or equal to about 100, including less than or equal to about 50, less than or equal to about 40, less than or equal to about 30, less than or equal to about 20, less than or equal to about 10, or less than or equal to about 1 micron. Useful ranges for the effective diameter of a preponderance of the multiplicity of droplets can be selected from any value between and inclusive of about 1 micron to about 100 microns. Non-limiting examples of such ranges can include from about 1 micron to about 100 microns, from about 10 microns to about 100 microns, from about 20 microns to about 100 microns, from about 30 microns to about 100 microns, from about 40 microns to about 100 microns, from about 50 microns to about 100 microns, or from about 20 microns to about 30 microns.

In another embodiment, more than three aqueous compositions, including one or more aqueous compositions consisting essentially of water can be dispersed into the volumetric space.

In another embodiment, the invention provides a disinfecting system for disinfecting a surface within a volumetric space, comprising a) a housing, b) a first container for a first liquid, associated with the housing; c) a second container for a second liquid, associated with the housing; d) a nozzle attached to the housing, in liquid communication with at least one of the first container and the second container, for dispensing a stream of droplets of at least one of the first liquid and the second liquid; e) an optional means for imparting an electrostatic charge to at least the first liquid during dispensing from the nozzle; and f) a microprocessor including a memory and programming, configured for dispensing a preselected mass or volumetric amount of the first liquid and a preselected mass or volumetric amount of the second liquid. Optionally the disinfecting system can also include g) a timing mechanism for controlling an amount of time between the dispensing of the first liquid, and the dispensing of the second liquid.

In further embodiments, the disinfecting system further comprises a third container for a third liquid, associated with the housing, wherein the nozzle is in liquid communication with at least one of the first container, the second container, or the third container, for dispensing a stream of droplets of at least one of the first liquid, the second liquid, and the third liquid into a volumetric space; the microprocessor further includes memory and programming configured for dispensing a preselected amount of the third liquid; and the timing mechanism further controls the amount of time between dispensing the second liquid and the third liquid.

In one embodiment, a single nozzle can be in selective liquid communication with the first container, the second container, or a third or another container. In another embodiment, a separate nozzle can be used for the second container or a third or other container.

In another embodiment, the disinfecting system further comprises a means for illuminating the volumetric space or the surfaces to be disinfected, with a wavelength consisting essentially of ultraviolet light.

These and other embodiments of the present invention will be apparent to one of ordinary skill in the art from the following detailed description.

BRIEF DESCRIPTION OF THE FIGURES

FIG. 1 shows a photograph of the commercial electrospray device according to the prior art.

FIG. 2 shows the dispersion and distribution of identically electrostatically-charged droplets onto a surface in need of disinfecting.

FIG. 3 shows a photograph of the interior of a passenger compartment of a train.

FIG. 4 shows a photograph of the exterior of a metal shipping container.

FIG. 5 shows a sketch of a sterile environment in an operating room.

FIG. 6 shows a sketch of potential surfaces to disinfect in hospital patient room.

DETAILED DESCRIPTION OF THE INVENTION

Figure 7:
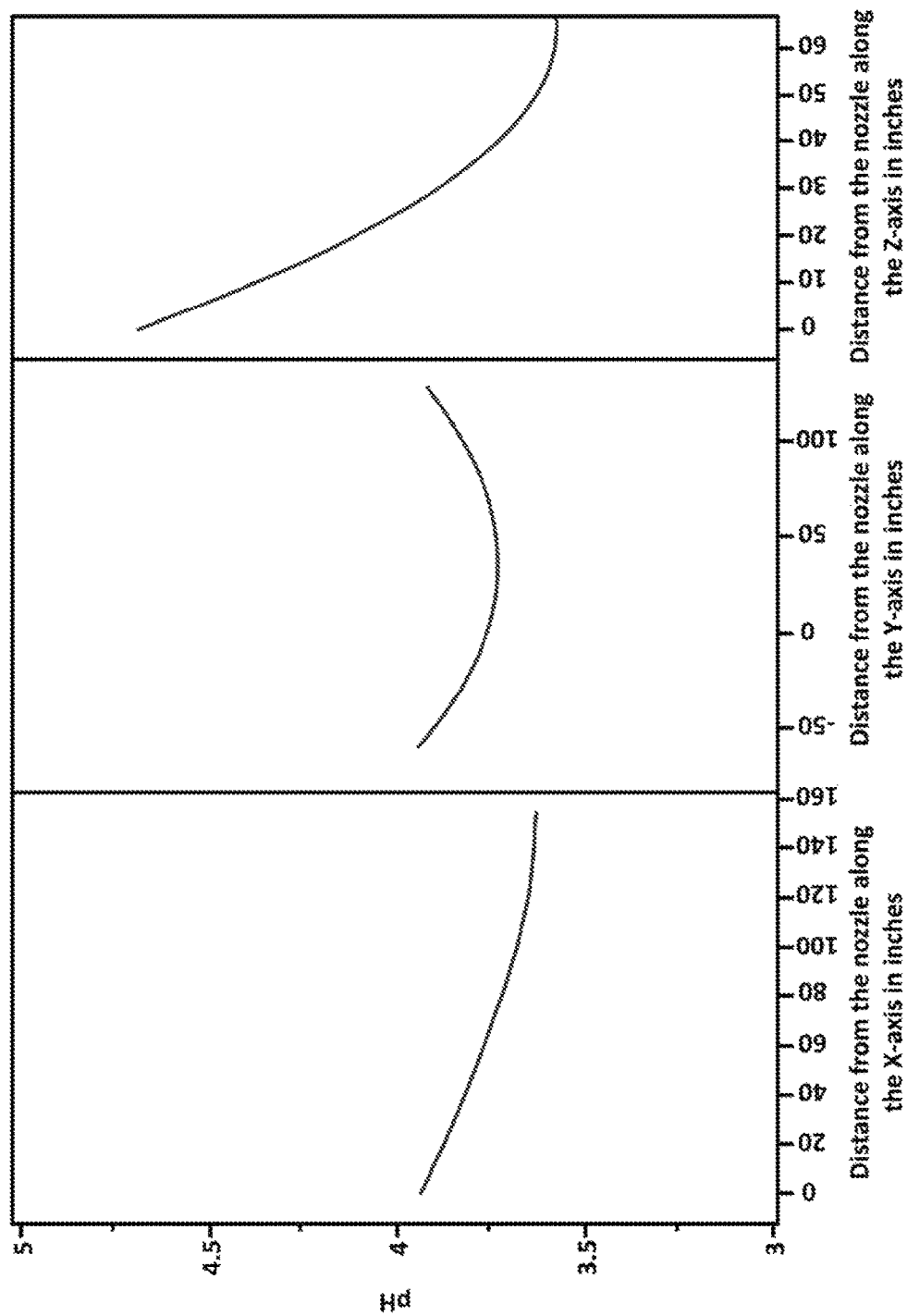
FIG. 7 shows plots illustrating the distribution of acetic acid as a function of changes in x, y, and z direction from the nozzle on an electrospray device.

The present disclosure includes a method and a system for sterilizing rooms, volumetric areas and spaces, and surfaces within those areas or spaces, particularly by generating peracids on those targets in situ by applying peracid reactant compounds in two or more separate applications. The methods and system described herein have several advantages over conventional disinfecting systems utilizing peracids to kill microbial populations. Other present methods and systems require the peracid to be formed prior to application of the peracid composition on targets to be disinfected, consequently leading to instability, degradation, and eventual loss of the peroxyacid activity and potency before the composition is ever applied. To account for this problem, conventional disinfecting methods and systems require adding additional peracid reactants or stabilizers to the reaction mixture to stabilize the peroxyacid before the composition is applied. In contrast, a method and system of the present invention do not require stabilizers because the peracid reactants are applied individually and the peracid is formed directly on the target surface after the reaction ingredients are added sequentially.

It should be understood that while reference is made to exemplary embodiments and specific language is used to describe them, no limitation of the scope of the invention is intended. Further modifications of the methods and system described herein, as well as additional applications of the principles of those inventions as described, which would occur to one skilled in the relevant art and having possession of this disclosure, are to be considered within the scope of this invention. Furthermore, unless defined otherwise, all technical and scientific terms used herein have the same meaning as commonly understood by one of ordinary skill in the art to which embodiments of this particular invention pertain. The terminology used is for the purpose of describing those embodiments only, and is not intended to be limiting unless specified as such.

Definitions

As used in this specification and in the claims, the singular forms "a," "an," and "the" include plural referents unless the content clearly dictates otherwise.

The term, "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Similarly, whether or not a claim is modified by the term, "about," the claims included equivalents to the quantities recited.

As used herein, the term, "aqueous composition," refers to a combination of liquid components that includes water. Most commonly, aqueous compositions are synonymous with the term "solution" as it is commonly used in the art for this invention. However, depending on the identity of components in the composition in addition to water, "aqueous compositions" can also encompass mixtures, emulsions, dispersions, suspensions or the like. Furthermore, while water must be present, it need not comprise the majority of the aqueous composition.

As used herein, the terms, "biocide" and "biocidal compound," refer to chemical substances intended to destroy, deter, render harmless, or exert a controlling effect on any organisms that are harmful to human or animal health or that cause damage to natural or manufactured products. Non-limiting examples of biocides include peroxide compounds, organic acids, peracids, alcohols, manuka honey, and essential oils, and natural biocidal compounds.

The term, "effective diameter," refers to either the geometric diameter of a spherical droplet, or of the distance from side-to-side of a distorted spherical droplet at the droplet's widest point.

The term, "effective uniform thickness" refers to target or ideal thickness of a liquid onto a surface where the mass or volume of a liquid deposited onto the surface has a substantially uniformly thickness.

The terms, "essential oil" or "spice oil," refer to concentrated natural products produced by and extracted from aromatic plants for their antimicrobial properties based on interactions with a variety of cellular targets.

As used herein, the phrase, "food processing surface" refers to a surface of a tool, a machine, equipment, a shipping container, railcar, structure, building, or the like that is employed as part of a food transportation, processing, preparation, or storage activity. Examples of food processing surfaces include surfaces of food processing or preparation equipment (e.g. slicing, canning, or transport equipment, including flumes), of food processing wares (e.g. utensils, dishware, wash ware, and bar glasses), and of floors, walls, or fixtures of structures in which food processing occurs.

Food processing surfaces are found and employed in food anti-spoilage air circulation systems, aseptic packaging sanitizing, food refrigeration and cooler cleaners, and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition that is edible with or without further preparation. Food products include meat (e.g. red meat and pork), seafood, poultry, produce (e.g. fruits and vegetables), eggs, living eggs, egg products, ready-to-eat food, wheat, seeds, roots, tubers, leaves, stems, corns, flowers, sprouts, seasonings, or a combination thereof. The term, "produce," refers to food products such as fruits and vegetables and plants or plant-derived materials that are typically sold uncooked and, often, unpackaged, and that can sometimes be eaten raw.

The terms, "free" or "substantially free" refers to the total absence or near total absence of a particular compound in a composition, mixture, or ingredient.

The term, "health care surface" refers to a surface of a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, nursing home, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term, "instrument," refers to the various medical or dental instruments or devices that can benefit from cleaning with a composition according to the present invention. As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the phrase, "organic acid," refers to any acid that is capable of forming a peracid that is effective as a disinfecting agent.

As used herein, the terms, "peracid" or "peroxyacid" refer to any acid having the hydrogen of a hydroxyl group replaced by a perhydroxyl group. Oxidizing peracids are referred herein as peroxycarboxylic acids.

As used herein, the phrase, "peracid reactant compound" refers to a reactant compound that will react to form a peracid on the target surface in situ.

As used herein, the term, "peroxide compound," refers to any compound that can react with an organic acid to form a peracid, including but not limited to hydrogen peroxide, metal peroxides, and ozone.

As used herein, the term, "polyhydric alcohol," refers to an alcohol that has two or more hydroxyl groups. Polyhydric alcohols suitable for use in the aqueous compositions include but are not limited to sugars, sugar alcohols, and non-aliphatic polyhydric alcohols such as phenols.

As used herein, the term, "reaction layer," refers to a layer formed on a surface to be disinfected when a multiplicity of droplets including a second reactant compound, for example a second peracid reactant compound, is deposited onto a coalesced layer formed on the surface by a multiplicity of droplets including a first reactant compound, for example, a first peracid reactant compound. The product of the two reactant compounds is formed in situ on the reaction layer.

As used herein, the term, "vapor," refers to a fluid phase or state in which a portion of an aqueous composition is substantially entirely in a gaseous state, as opposed to other embodiments in which there are a significant portion of liquid droplets of the aqueous composition suspended in the air.

The term, "weight percent," "percent by weight," "w/w," and other variations, as used herein, refer to the concentration of a substance as a weight of that substance divided by the total weight of the composition, multiplied by 100. It is understood that "percent," "%," and like terms are intended to be synonymous with "weight percent," "percent by weight," etc, rather than percent by volume of the composition.

In describing embodiments of the disinfecting methods and system in the present disclosure, reference will be made to "first" or "second" as they refer to aqueous compositions or peracid reactant compounds. Except when there is clear context that a specific order is intended, "first" and "second" are merely relative terms, and a "first" composition or reactant compound described could just as easily and conveniently be referred to as a "second" composition or reactant compound, and such description is implicitly included herein.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 0.5% to about 10% by weight includes not only the explicitly recited limits of 0.5% by weight and 10% by weight, but also individual weights such as 1% by weight and 5% by weight, and sub-ranges such as 2% to 8% by weight, 5% to 7% by weight, etc.

Embodiments of the Invention

In accordance with these definitions, several methods for disinfecting target surfaces within a volumetric space by forming a peracid on those surfaces in situ are provided. The potential applications for these methods are extraordinarily diverse, including but not limited to disinfecting food products and processing surfaces; health care surfaces and instruments; laboratories; restrooms; vehicles; schools; offices; public transportation; industrial, commercial, and homecare facilities; heating, ventilation, and air conditioning (HVAC) systems; and countless other areas and surfaces. This invention overcomes the deficiencies associated with forming peracids prior to applying them for sterilization, particularly with regard to the instability and safety of the peracid in solution.

While other sterilization methods attempt to solve the peracid stability and safety problem by including one or more additives in the reaction mixtures to promote the retention of the peracid in the system, many of these additives are expensive to produce and are not readily attainable for an average person with no connection to the chemical industry. In contrast, this invention harnesses the power of peracid chemistry to disinfect target surfaces while utilizing ingredients that have a very long shelf life and that are generally regarded as safe because one can obtain them at their local grocery or department store.

Without being limited by theory, it is believed that peracids are so effective as disinfectants because they are powerful oxidizing agents that can irreversibly damage proteins and DNA within microorganisms. Peracids are formed in an acid-catalyzed reaction when a strong oxidizing agent, such as a peroxide compound, comes into contact with an organic acid. For example, in a system that utilizes acetic acid as the organic acid, addition of a peroxide compound such as hydrogen peroxide can result in a reaction in which peracetic acid and water are produced in equilibrium as shown below:

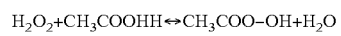

$$H_2O_2 + CH_3COOHH \leftrightarrow CH_3COO-OH + H_2O$$

Once the peracid is formed on the surface to be disinfected, it is strongly electrophilic. If there are no electron-rich sources in solution with the peracid, the excess water will drive equilibrium toward hydrolysis of the peracid and back into production of the parent acid. Additionally, as the parent acid becomes increasingly acidic, the resultant peracid similarly becomes more reactive. Thus, even though the resultant peracid could become an even better disinfectant under those conditions, it is also more unstable and likely to never reach the target surface, regardless of how immediately before application the individual components are mixed. Consequently, embodiments of this invention can similarly be more effective than the present art in industrial applications where stronger and more strictly-controlled components are used and cost is not an object.

The present invention provides a method of disinfecting a surface in need of disinfecting within a volumetric space, comprising the steps of: a) dispersing into the volumetric space a multiplicity of droplets of a first aqueous composition comprising a first peracid reactant compound that is either a peroxide compound or an organic acid, wherein the multiplicity of droplets of the first aqueous composition deposits onto the surface; and b) dispersing into the volumetric space a multiplicity of droplets of a second aqueous composition comprising a second peracid reactant compound that is the other of the first peracid reactant compound, wherein the multiplicity of droplets of the second aqueous composition deposits upon the surface and coalesces with the multiplicity of droplets of the first aqueous composition, thereby forming one or more composition pools upon the surface, and forming the peracid in situ within each composition pool, and disinfecting the surface.

In another embodiment, a method to disinfect surfaces in need of disinfecting within a volumetric space comprises the steps of dispersing into the volumetric space a multiplicity of droplets of a first aqueous composition comprising a first peracid reactant compound that is either a peroxide compound or an organic acid compound, wherein the first aqueous composition deposits and coalesces into a first aqueous composition layer upon the surface; and dispersing into the volumetric space a multiplicity of droplets of a second aqueous composition comprising a second peracid reactant compound that is the other of the first peracid reactant compound, wherein the second aqueous composition deposits onto the coalesced first aqueous composition layer to form a reaction layer upon the surface, thereby forming a peracid in situ within the reaction layer and disinfecting the surface, thereby forming a peracid in situ on the reaction layer and disinfecting the surfaces.

As long as a peracid is formed only on the surface to be disinfected, the effectiveness of the method is expected to be independent of the order in which the peracid reactant compounds are dispersed. Thus, the first peracid reactant compound can either be an organic acid or a peroxide compound, so long as the second peracid reactant compound is the opposite compound of that chosen to be the first peracid reactant compound. For example, the second peracid reactant compound is an organic acid if a peroxide compound is selected to be the first peracid reactant compound, and the second peracid reactant compound is a peroxide compound if an organic acid is selected to be the first peracid reactant compound. Although the compositions containing the peracid reactant compounds are generally mostly aqueous, water need not comprise the majority of the composition. Furthermore, any liquid carrier system that can facilitate the formation of the peracid from a peroxide compound and an organic acid can be used.

As illustrated in the examples below, control reactions in which only one peracid reactant compound is deposited onto a surface indicate that a peroxide compound, on its own, has a greater effect on the percent kill of bacteria than an organic acid. Without being limited by a particular theory, it is believed that the peroxide compound is more effective because peroxides are generally more reactive than organic acids, and thus bacterial defense systems are more sensitive to the presence of peroxides than organic acids. Thus, in some embodiments, the stoichiometric amount of the dispersed peroxide compound is equal to or greater than the stoichiometric amount of the dispersed organic acid. In other embodiments, the stoichiometric amount of the peroxide compound in the reaction layer is equal to or greater than the stoichiometric amount of the organic acid in the reaction layer.

In another embodiment, the peroxide compound can be any compound that can react with an organic acid to form a peracid. Generally, these will include but not be limited to hydrogen peroxide, metal peroxides, or ozone. In some embodiments, an aqueous composition containing a peroxide compound comprises at least about 0.1, including at least about 0.5, at least about 1, at least about 2, at least about 4, at least about 6, at least about 8, at least about 10, at least about 12, at least about 14, at least about 16, at least about 18, at least about 20, or at least about 25, percent, by weight, of the peroxide compound. In other embodiments, an aqueous composition containing a peroxide compound comprises less than or equal to about 25, including less than or equal to about 20, less than or equal to about 18, less than or equal to about 16, less than or equal to about 14, less than or equal to about 12, less than or equal to about 10, less than or equal to about 8, less than or equal to about 6, less than or equal to about 4, less than or equal to about 2, less than or equal to about 1, less than or equal to about 0.5, or less than or equal to about 0.1, percent, by weight. of the peroxide compound. Useful ranges can be selected from any value between and inclusive of about 0.1% to about 25% by weight of the peroxide compound. Non-limiting examples of such ranges can include from about 0.1% to about 25% by weight, from about 0.5% to about 25% by weight, from about 1% to about 25% by weight, from about 2% to about 25% by weight, from about 4% to about 25% by weight, from about 6% to about 25% by weight, from about 8% to about 25% by weight, from about 10% to about 25% by weight, from about 12% to about 25% by weight, from about 14% to about 25% by weight, from about 16% to about 25% by weight, from about 18% to about 25% by weight, from about 20% to about 25% by weight, from about 0.5% to about 20% by weight, from about 1% to about 18% by weight, from about 2% to about 16% by weight, from about 5% to about 15% by weight, or from about 7% to about 12% by weight. In some embodiments, the aqueous composition comprises about 10% by weight of the peroxide compound. In preferred embodiments, the peroxide compound is hydrogen peroxide.

The organic acid can be any organic acid that can effectively form a peracid upon reacting with a peroxide compound. In some embodiments, the organic acid can be any organic acid that is capable of forming a peracid upon reacting with a peroxide compound. Generally, these will include but not be limited to carboxylic acids. Non-limiting examples of carboxylic acids which can be used include formic acid, acetic acid, citric acid, succinic acid, oxalic acid, propanoic acid, lactic acid, butanoic acid, pentanoic acid, octanoic acid, amino acids, and mixtures thereof. In some embodiments, an aqueous composition containing an organic acid comprises at least about 0.5, including at least about 1, at least about 2, at least about 5, at least about 10, at least about 15, at least about 20, at least about 25, at least about 30, at least about 35, at least about 40, at least about 45, or at least about 50, percent, by weight. of the organic acid. In other embodiments, an aqueous composition containing an organic acid comprises less than or equal to about 50, including less than or equal to about 45, less than or equal to about 40, less than or equal to about 35, less than or equal to about 30, less than or equal to about 25, less than or equal to about 20, less than or equal to about 15, less than or equal to about 10, less than or equal to about 5, less than or equal to about 2, less than or equal to about 1, or less than or equal to about 0.5, percent, by weight, of the organic acid. Useful ranges can be selected from any value between and inclusive of about 0.5% to about 50% by weight of the organic acid. Non-limiting examples of such ranges can include from about 0.5% to about 50% by weight, from about 1% to about 50% by weight, from about 2% to about 50% by weight, from about 5% to about 50% by weight, from about 10% to about 50% by weight, from about 15% to about 50% by weight, from about 20% to about 50% by weight, from about 25% to about 50% by weight, from about 30% to about 50% by weight, from about 35% to about 50% by weight, from about 40% to about 50% by weight, from about 45% to about 50% by weight, from about 1% to about 35% by weight, from about 2% to about 20% by weight, or from about 4% to about 12% by weight. In some embodiments, the aqueous composition comprises about 10% by weight of the organic acid. In preferred embodiments, the organic acid is acetic acid.

As described above, the synthesis of peracids from an organic acid and a peroxide compound is an acid-catalyzed process (see Zhao, X., et al., (2007) *Journal of Molecular Catalysis A* 271:246-252). Typically, organic acids such as acetic acid and the others listed above have at least one carboxylate functional group with an acidic pKa value less than or equal to about 7, making such compounds suitable for reacting with a peroxide compound to produce a peracid. Some organic acids, such as citric acid, have multiple carboxylic acid groups which each have a pKa value below 7 and can thus react with a peroxide compound to form the peracid product. However, organic acids that possess carboxylic acid functional groups with pKa values above 7 can be used as also substrates so long as at least one of the carboxylic acid functional groups has a pKa value less than or equal to about 7. Consequently, in some embodiments, the pH of the composition comprising the organic acid is less than or equal to about 7. In further embodiments, the pH of the reaction layer is less than or equal to about 7.

In another embodiment, at least about 90, 95, 97, 98, or 99 percent of the aqueous compositions are dispersed as a multiplicity of droplets. In further embodiments, essentially 100 percent of the aqueous compositions are dispersed as a multiplicity of droplets.

In another embodiment, the effective diameter of the droplets of an aqueous composition is controlled to which enable the droplets to remain in the air long enough to overcome gravity and reach all of the surfaces to be disinfected within the volumetric space to be disinfected. This can be particularly advantageous when there are a large number and/or a diverse arrangement of surfaces within the volumetric space that need to be disinfected. On the other hand, issues can also potentially arise when the effective diameter of the droplets is small. It is known that airborne droplets can be inhaled and retained in the deep lung at effective diameters less than about eight to about ten microns, as illustrated in Drug and Biological Development: From Molecule to Product and Beyond, edited by Ronald Evens, pg. 210 and applicable sections, 2007, hereby incorporated by reference in its entirety. Additionally, droplets that are very small have the potential to linger within the volumetric space for extended periods without depositing on the surfaces to be disinfected.

Thus, the preponderance of the multiplicity of droplets can be controlled to have an effective diameter of at least about 1, including at least about 5, at least about 10, at least about 15, at least about 20, at least about 25, at least about 30, at least about 35, at least about 40, at least about 45, at least about 50, at least about 60, at least about 70, at least about 80, at least about 90, or at least about 100, microns. In other embodiments, the preponderance of the multiplicity of droplets have an effective diameter of less than or equal to about 100, including than or equal to about 90, than or equal to about 80, than or equal to about 70, than or equal to about 60, than or equal to about 50, than or equal to about 45, than or equal to about 40, than or equal to about 35, than or equal to about 30, than or equal to about 25, than or equal to about 25, than or equal to about 20, than or equal to about 15, than or equal to about 10, or than or equal to about 5, microns. Useful ranges for the effective diameter of a preponderance of the multiplicity of droplets can be selected from any value between and inclusive of about 1 micron to about 100 microns. Non-limiting examples of such ranges can include from about 1 micron to about 100 microns, from about 5 microns to about 100 microns, from about 10 microns to about 100 microns, from about 15 microns to about 100 microns, from about 20 microns to about 100 microns, from about 25 microns to about 100 microns, from about 30 microns to about 100 microns, from about 35 microns to about 100 microns, from about 40 microns to about 100 microns, from about 45 microns to about 100 microns, from about 50 microns to about 100 microns, from about 60 microns to about 100 microns, from about 70 microns to about 100 microns, from about 80 microns to about 100 microns, from about 90 microns to about 100 microns, from 3 microns to about 75 microns, or from about 10 microns to about 25 microns. In embodiments in which a person is intentionally present in the volumetric space or access to the volumetric space cannot be restricted, the effective diameter of a preponderance of the droplets can be maintained to be above about 10 microns in order to avoid deep lung penetration, particularly about 15 microns. In other embodiments in which human access to a volumetric space is not a concern, the effective diameter of a preponderance of the multiplicity of droplets can be any diameter that facilitates distribution, deposition, and coalescence of the droplets onto a surface or surfaces to be disinfected, including such effective diameters as listed above.

In another embodiment, methods of the present invention can further comprise the step of allowing a time sufficient for the droplets to distribute throughout the volumetric space prior to depositing onto the surfaces to be disinfected. In other embodiments, the time sufficient is the time it takes for the dispersed aqueous composition to deposit and coalesce into a layer onto substantially all of the intended surfaces to disinfect within a volumetric area. The time sufficient for the multiplicity of droplets of each of the aqueous compositions to disperse into a volumetric space, and to deposit and coalesce into a layer upon the surface or surfaces to be disinfected, can depend on several factors, including but not limited to: the size and velocity of the droplets as they are dispersed; the volumetric size and humidity of the volumetric space; and the identity and concentration of the components within the aqueous composition. With regard to droplet size, the time sufficient for the droplets to reach and coalesce upon the surfaces to be disinfected is approximately inversely proportional to the size of the droplet. Thus, when a droplet is small, for example with an effective diameter of about 1 to about 2 microns, more time is needed to deposit onto a surface than when the droplet is large, for example with an effective diameter of about 50 to about 100 microns or more.

However, while large droplets are functionally adequate for disinfecting multiple surfaces in larger volumetric spaces such as rooms or shipping containers, it has been observed that the ability of the droplets to distribute and form a coalesced layer on a diversity of surfaces within the volumetric space becomes compromised once the effective diameter of the droplets reaches about 20 microns or more. Instead, droplet sizes above 20 microns are more suited for disinfecting a portion or the entirety of a selected surface or a limited number of selected surfaces within a volumetric space.

In other embodiments, the time sufficient can be defined by discrete passage of time in between the sequential dispersion of successive aqueous compositions. In further embodiments, the time sufficient to allow the aqueous composition to distribute throughout the volumetric space and deposit onto the surfaces to be disinfected is at least about 1 minute, including at least about 5 minutes, or at least about 10 minutes, or at least about 20 minutes, or at least about 30 minutes, and up to at least about 60 minutes, including up to about 30 minutes, or up to about 20 minutes, or up to about 15 minutes.

In another embodiment, a time sufficient for droplets to distribute throughout the volumetric space and deposit on the surfaces to be disinfected can be utilized for one or more of the dispersed aqueous compositions. In another embodiment, the method further comprises the step of allowing a first time sufficient for the multiplicity of droplets of the first aqueous composition to distribute throughout the volumetric space prior to depositing and coalescing into a layer upon the surface. In other embodiments, the method further comprises the step of allowing a second time sufficient for the multiplicity of droplets of the second aqueous composition to distribute throughout the volumetric space prior to depositing onto the coalesced first aqueous composition layer and forming a reaction layer upon the surface. In further embodiments, the second time sufficient is the time sufficient for substantially all of the second peracid reactant compound to combine and react with substantially all of the first peracid reactant compound within the reaction layer.

In another embodiment, a step allowing a time sufficient for droplets of the first aqueous composition to distribute and deposit onto the surface to form a coalesced first aqueous composition layer and a step allowing a time sufficient for droplets of the second aqueous composition to distribute throughout the volumetric space and deposit onto the coalesced first aqueous composition layer to form a reaction layer can be included in the same disinfection method. Thus, in some embodiments, the method comprises the steps of a) dispersing into the volumetric space a multiplicity of droplets of a first aqueous composition comprising a first peracid reactant compound that is either a peroxide compound or an organic acid compound capable of reacting with a peroxide compound to form a peracid; b) allowing a time sufficient for the first aqueous composition to distribute throughout the volumetric space, and to deposit and coalesce into a layer upon the surface; c) dispersing into the volumetric space a multiplicity of droplets of a second aqueous composition comprising a second peracid reactant compound that is the other of the first peracid reactant compound; and d) allowing a second time sufficient for the droplets of the second aqueous composition to deposit onto the coalesced layer of the first aqueous composition to form a reaction layer, thereby forming a peracid in situ on the reaction layer and disinfecting the surface. In further embodiments, the method can further comprise the step of allowing a third time sufficient when dispersing droplets of a third aqueous composition consisting essentially of water into the volumetric space, in order for droplets of the third aqueous composition to distribute throughout the volumetric space and/or deposit onto the surfaces to be disinfected, as described below.

In another embodiment of the invention, the multiplicity of droplets of the first aqueous composition that are dispersed into the volumetric space can remain as a multiplicity of droplets when they are deposited onto the surfaces to be disinfected. In further embodiments, the multiplicity of droplets of the second aqueous composition can deposit directly onto the multiplicity of droplets of the first aqueous composition on the surface. In other further embodiments, the multiplicity of deposited droplets of the second aqueous composition can coalesce with the multiplicity of droplets of the first aqueous composition upon depositing onto the surface, forming one or more reaction composition pools, and alternatively, into an aqueous reaction layer, upon the surface, and forming the peracid in situ within each reaction composition pool or aqueous reaction layer.

In another embodiment, the multiplicity of droplets of the first aqueous composition that are dispersed into the volumetric space can deposit onto the surface and coalesce into a plurality of non-contiguous first aqueous composition pools upon the surface. In such embodiments, the multiplicity of droplets of the second aqueous composition can deposit onto the plurality of non-contiguous first aqueous composition pools to form a plurality of reaction composition pools upon the surface. In further embodiments, the plurality of reaction composition pools coalesce into a single, coalesced reaction layer upon the surface, and forming the peracid in situ within the single coalesced reaction layer.

In another embodiment, once the multiplicity of droplets of the first aqueous composition is deposited onto a surface to be disinfected, the droplets preferably coalesce into a single layer having a substantially uniform thickness, in order to provide maximal coverage on the surface. In preferred embodiments, the actual deposited thickness of the coalesced layer should be minimized while also substantially covering all exposed and unexposed locations on the surface. The thickness of the coalesced layer is dependent on both the size and surface tension of the multiplicity of droplets. In some embodiments where the multiplicity of droplets consists only of peroxide compounds or organic acids in an aqueous solution, the droplets can possess a surface tension close to that of pure water, which is about 72 dyne/cm at 20° C. In this situation, the coalesced layer may be thicker because the droplets will narrowly spread after being deposited upon the surface. Thus, more composition is needed to completely cover and disinfect the entire surface.

Conversely, the multiplicity of droplets may additionally include non-aqueous compounds that lower the composition's surface tension. For example, pure ethanol has a surface tension of about 22.27 dyne/cm at 20° C. In this situation, the composition droplets with the lower surface tension will more widely spread, creating a thinner coalesced layer that requires less of the composition to completely cover and disinfect the surface.

Thus, in another embodiment, the coalesced layer can have an effective uniform thickness, and preferably an actual uniform thickness, of at least about 1, including at least about 2, at least about 3, at least about 5, at least about 8, at least about 10, at least about 15, or at least about 20, microns. In other embodiments, the coalesced layer can have an effective uniform thickness, and preferably an actual uniform thickness, of less than or equal to about 20, including less than or equal to about 15, less than or equal to about 10, less than or equal to about 8, less than or equal to about 5, less than or equal to about 3, less than or equal to about 2, or less than or equal to about 1, microns. Useful ranges for the substantially uniform thickness of a coalesced layer of an aqueous composition can be selected from any value between and inclusive of about 1 micron to about 20 microns. Non-limiting examples of such ranges can include from about 1 micron to about 20 microns, from about 2 microns to about 20 microns, from about 3 microns to about 20 microns, from about 5 microns to about 20 microns, from about 8 microns to about 20 microns, from about 10 microns to about 20 microns, from about 15 microns to about 20 microns, or from about 3 microns to about 8 microns.

In another embodiment, one or more alcohols can be added to one or both of the aqueous compositions to decrease the surface tension of the compositions and the droplets deposited on the surface to be disinfected. The alcohol contained in either aqueous composition promotes a thinner coalesced layer without having to reduce the droplet size to a smaller effective diameter, where a sufficiently small diameter could potentially result in deep lung penetration for any persons or animals in the area or volumetric space. Furthermore, some alcohols also independently provide biocidal activity separate from the peracid. Therefore, using alcohols in combination with forming the peracid in situ on the surface to be disinfected may provide additive effects on the antimicrobial activity as compared to reaction layers which only contain a peroxide compound and an organic acid.

Although an alcohol in liquid form can be used at high concentrations (70% by weight or above) to sterilize instruments or surfaces, many alcohols are combustible at those same concentrations when volatilized, especially as the temperature of the area or volumetric space is increased. Thus, in another embodiment, an aqueous composition comprising an alcohol can comprise at least about 0.05, 0.1, 1, 5, 10, 15, 20, 25, 30, 40, 50, 60, or 70 percent by weight of the alcohol. In other embodiments, an aqueous composition containing an alcohol comprises less than or equal to about 0.05, 0.1, 1, 5, 10, 15, 20, 25, 30, 40, 50, 60, or 70 percent by weight of the alcohol. Useful ranges can be selected from any value between and inclusive of about 0.05% to about 70% by weight of the alcohol. Non-limiting examples of such ranges can include from about 0.05% to about 70% by weight, from about 0.1% to about 70% by weight, from about 1% to about 70% by weight, from about 5% to about 70% by weight, from about 10% to about 70% by weight, from about 15% to about 75% by weight, from about 20% to about 70% by weight, from about 25% to about 70% by weight, from about 30% to about 70% by weight, from about 40% to about 70% by weight, from about 50% to about 70% by weight, from about 60% to about 70% by weight, from about 1% to about 25% by weight, or from about or 10% to about 20% by weight of the alcohol. In some embodiments, an aqueous composition comprising an alcohol can comprise about 15% by weight of the alcohol.

The alcohol present in an aqueous composition can be a single alcohol or a combination of multiple alcohols. An alcohol can include aliphatic alcohols and other carbon-containing alcohols having from 1 to 24 carbons. The alcohol can be selected from a straight-chained or completely saturated alcohol or other carbon-containing alcohols, including branched aliphatic alcohols, alicyclic, aromatic, and unsaturated alcohols. Polyhydric alcohols can also be used alone or in combination with other alcohols. Non-limiting examples of polyhydric alcohols which can be used in the present disclosure include ethylene glycol (ethane-1,2-diol) glycerin (or glycerol, propane-1,2,3-triol), propane-1,2-diol, polyvinyl alcohol, sorbitol, other polyols, and the like. Other non-aliphatic alcohols may also be used including but not limited to phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z, 12Z-octadecadien-1-ol), elaidyl alcohol (9E-octadecen-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), and combinations thereof.

In another embodiment, for practical considerations, methanol, ethanol, isopropanol, t-butanol, and denatured alcohols can be used because of their properties and cost. The alcohol can be selected to satisfy the requirements for food-grade and food-safe systems. However, many alcohols, particularly primary alcohols, for example methanol and ethanol, can form an ester in a side reaction with an organic acid. As a non-limiting example, ethanol and acetic acid can form ethyl acetate at room temperature, particularly under acidic pH conditions. Consequently, in preferred embodiments, isopropanol and t-butanol can be chosen because side reactions with the organic acid are not favored because isopropanol and t-butanol are secondary and tertiary alcohols, respectively.

In other embodiments, additional compounds can be included in either aqueous composition to enhance or supplement the effectiveness of the peracid generated in situ on the surface to be disinfected. Such compounds can include one or more natural biocides, such as manuka honey and essential oils, and/or natural biocidal compounds typically found within manuka honey and essential oils, such as methylglyoxal, carvacrol, eugenol, linalool, thymol, p-cymene, myrcene, borneol, camphor, caryophillin, cinnamaldehyde, geraniol, nerol, citronellol, and menthol, including combinations thereof. Honey, particularly manuka honey, has long been known to have biocidal properties. The anti-bacterial properties of methylglyoxal, the primary component of manuka honey, has been described previously (see Hayashi, K., et al., (April 2014) *Frontiers in Microbiology*, 5 (180):1-6, hereby incorporated by reference in its entirety). Methylglyoxal has been shown to be effective against multidrug resistant bacteria, including methicillin-resistant *Staphylococcus aureus* (MRSA), multidrug-resistant *Pseudomonas aeruginosa*, and pathogenic *Escherichia coli* with minimum inhibitory concentrations (MIC) as low as 0.005% by weight.

In other embodiments, essential oils can be included in either aqueous composition. Essential oils have been widely-used in medicines throughout human history, and are particularly known to have antimicrobial activity at concentrations as low as 0.001% by weight, as described in Effect of Essential Oils on Pathogenic Bacteria, Pharmaceuticals, pg. 1451-1474, Volume 6, 2013, and Antimicrobial Activity of Some Essential Oils Against Microorganisms Deteriorating Fruit Juices, Mycobiology, pg. 219-229, Volume 34, 2006, both of which are hereby incorporated by reference in their entirety. The use of essential oils as components in disinfectants is described in U.S. Pat. No. 6,436,342, the disclosure of which is incorporated by reference in its entirety. Non-limiting examples of essential oils that can be included in one or more of the aqueous compositions include the essential oils of oregano, thyme, lemongrass, lemons, oranges, anise, cloves, aniseed, cinnamon, geraniums, roses, mint, peppermint, lavender, citronella, eucalyptus, sandalwood, cedar, rosmarin, pine, vervain fleagrass, and ratanhiae.

In addition to their antimicrobial properties, several essential oils produce odors that are pleasing to subsequent users of the disinfected room or volumetric space after the method has been completed. Accordingly, one or more natural biocides or natural biocidal compounds, particularly essential oils and/or their chemical components, can be included in an aqueous composition at a concentration less than the MIC. Thus, in another embodiment, an aqueous composition can comprise one or more natural biocides or natural biocidal compounds at a concentration of at least about one of 0.001, 0.005, 0.01, 0.05, 0.1, 0.25, 0.5, or 1, percent, by weight. In other embodiments, an aqueous composition can comprise one or more natural biocides or natural biocidal compounds at a concentration of less than or equal to about one of 0.001, 0.005, 0.01, 0.05, 0.1, 0.25, 0.5, or 1, percent, by weight. Useful ranges can be selected from any value between and inclusive of about 0.001% to about 1% by weight of the natural biocide or natural biocidal compound. Non-limiting examples of such ranges can include from about 0.001% to about 1% by weight, from about 0.005% to about 1% by weight, from about 0.01% to about 1% by weight, from about 0.05% to about 1% by weight, from about 0.1% to about 1% by weight, from about 0.25% to about 1% by weight, from about 0.5% to about 1% by weight, from about 0.01% to about 0.5% by weight, or from about 0.06% to about 0.3% by weight of the natural biocide or natural biocidal compound.

Without being bound by a particular theory, the effective uniform thickness of a coalesced liquid layer or reaction layer can be optimized according to the desired concentrations of the peracid reactant compounds or any other component of the aqueous compositions. In other embodiments, the concentrations of the peracid reactant compounds or other components can be optimized according to the desired effective uniform thickness. For instance, in some embodiments in which the concentration of the peracid reactant compounds or other reaction components are desired to be relatively dilute, then the volume of the aqueous compositions dispersed can be adjusted accordingly in order to increase the effective uniform thickness of the reaction layer (thus, the total amount of peracid reactant compound present) and achieve a desired microbial kill. Such an embodiment can be useful in situations in which stock solutions used to form one or more of the aqueous compositions are less concentrated, as with acetic acid or hydrogen peroxide that can be purchased by consumers at their local grocery store or pharmacy. Conversely, in other embodiments in which industrial-grade stock solutions are available, a relatively higher peracid reactant concentration is desired, or the volumetric space is relatively large, the volume of the dispersed aqueous compositions can be adjusted in order to form a relatively thinner reaction layer. Those skilled in the art possess the requisite knowledge to determine the concentration of the peracid reactant compounds or other components to determine the volume of the aqueous compositions to disperse to form a reaction layer with a desired effective uniform thickness, based on factors such as the concentration of stock solutions, desired microbial kill, and the volume inside the volumetric space, among other factors.

An advantage of the components described above, including the peracid reactant compounds, alcohols, and natural biocidal compounds, is that they are easily volatilized after the sterilization is complete. Such embodiments include situations in which high turnover is required in order to enable people to return to the volumetric space as quickly as possible after the sterilization method is completed. In embodiments where the coalesced layer on the surfaces to be disinfected has an effective uniform thickness of about 1 micron to about 20 microns, the aqueous compositions can rapidly evaporate from treated surfaces, obviating the need for additional treatments to remove unwanted components and waste products, and facilitating a faster turnover of the area in which the surfaces are located. Accordingly, such embodiments require that non-volatile salts and high-molecular weight materials be used sparingly or omitted completely in order to promote high turnover of the volumetric space containing the surfaces to be disinfected. In some embodiments, the aqueous compositions have a volatility such that at least about 90, including at least about 95, at least about 99, at least about 99.5, at least about 99.7, or at least about 99.9, percent, by weight, of the reaction layer can evaporate within 30 minutes of being formed.

To enhance the volatility of the aqueous compositions after they are deposited on one or more surfaces, the individual components of each of the aqueous compositions can be selected to have a relatively higher standard vapor pressure compared to less labile components that remain on surfaces long after they are disinfected. The standard vapor pressures of several typical components of the aqueous compositions are listed below in Table 1. It is noted that hydrogen peroxide on the surface that has not reacted with the organic acid would subsequently decompose into water and oxygen gas, each of which is much more volatile than hydrogen peroxide itself

TABLE 1

Standard Vapor Pressures of Common Aqueous Composition Components at 20° C.

| Compound Name | Vapor Pressure (mmHg) |
| --- | --- |
| Water | 17.5 |
| Acetic Acid | 11.3 |
| Hydrogen Peroxide | 1.5 |
| Ethanol | 43.7 |
| Isopropanol | 44.0 |
| t-Butanol | 31.0 |

Thus, in another embodiment, one or both of the aqueous compositions can be formulated so at least about 99.0, or at least about 99.5, or at least about 99.9, percent, of the components, by weight of the aqueous composition, have a standard vapor pressure of at least 1.0 mm Hg at 20° C. In further embodiments, one or both of the aqueous compositions can be formulated so that essentially 100% of the components by weight of the aqueous composition have a vapor pressure of at least about 1.0 mm Hg at 20° C.

In other embodiments, however, it can be advantageous to include additional components in at least one of the aqueous compositions in order to supplement or enhance the disinfection of surfaces within a volumetric space, particularly in situations in which the volatility of the aqueous compositions once they have been deposited onto surfaces is not a concern. Such additional components can include, but are not limited to: surfactants, polymers, chelators, metal colloids and/or nanoparticles, oxidizers, and other chemical additives, including combinations thereof, the use of which is described in U.S. Pat. Nos. 6,692,694, 7,351,684, 7,473,675, 7,534,756, 8,110,538, 8,679,527, 8,716,339, 8,772,218, 8,789,716, 8,987,331, 9,044,403, 9,192,909, 9,241,483, and 9,540,248, as well as U.S. Patent Publications 2008/0000931; 2013/0199539; 2014/0178249; 2014/0238445; 2014/0275267; and 2014/0328949, the disclosures of which are incorporated by reference in their entireties.

In another embodiment, supplemental components such as the surfactants, polymers, chelators, metal colloids and/or nanoparticles, oxidizers, and other chemical additives described above can be delivered or dispersed within one or more aqueous compositions in addition to the first or second aqueous compositions as described above that contain peracid reactant compounds. Over the course of a single treatment, three or more aqueous compositions can be utilized and dispersed according to the methods of the present invention. Accordingly, within such embodiments, peracid reactant compounds can be delivered by any two separate aqueous compositions dispersed during methods, and do not necessarily have to be included in the "first" or "second" aqueous composition dispersed so long as a peroxide compound and an organic acid are dispersed as part of two separate compositions and a peracid is formed in situ on a surface to be disinfected.

In a further embodiment, the one or more additional aqueous compositions can comprise at least one aqueous composition consisting essentially of water. Dispersing compositions consisting essentially of water opens up several optional possibilities with regard to pre-treatment, intermediate, and finishing steps that can be implemented in conjunction with the methods presented herein. For instance, in some embodiments, a method can further include the step of dispersing into the volumetric space a pre-treating composition consisting essentially of water, in order to increase the humidity in the volumetric space to maintain the droplets of aqueous compositions containing peracid reactant compounds and inhibit or prevent them from being lost or evaporated into the environment before the peracid reactant compounds reach the surface to be disinfected. In some embodiments, sufficient volume of a pre-treatment composition consisting essentially of water can be dispersed into the volumetric space in order to raise the relative humidity in the volumetric space to at least about 50, including at least about 60, or 70, or 80, or 90, or 95, or 99, percent. In further embodiments, sufficient volume or mass of a pre-treatment composition consisting essentially of water can be dispersed into the volumetric space in order to raise the relative humidity in the volumetric space to at least about 90 percent. Those skilled in the art can determine the necessary volume of a pre-treatment composition consisting of essentially of water to disperse in order to reach the desired relative humidity based on the atmospheric conditions within the volumetric space as well as the Cartesian dimensions of the volumetric space.

In other embodiments, the method can include a step of dispersing into the volumetric space an intermediate composition consisting essentially of water, after the dispersion of the first aqueous composition comprising the first peracid reactant compound, in order to coalesce with and enhance deposition of any excess or lingering droplets of the first aqueous composition from the air. In another embodiment, the method can include a step of dispersing into the volumetric space a finishing composition consisting essentially of water, after the dispersion and deposition of the aqueous composition comprising the second peracid reactant compound to coalesce with and enhance deposition of any excess or lingering droplets of the second aqueous composition. Removing excess or lingering suspended droplets of any aqueous composition containing a peracid reactant compound can render the volumetric space substantially free of any of the chemical components dispersed during disinfection.

The droplet size of any of the pre-treating, intermediate, or finishing compositions can be controlled to enhance the scavenging of lingering or suspended droplets containing a peracid reactant compound, as well as promote rapid deposition onto surfaces below. In some embodiments, the effective diameter of a preponderance of the droplets of an aqueous composition consisting essentially of water is at least about 1, or 10, or 20, or 30, or 40, or 50, or 100, microns. Preferably, the effective diameter of a preponderance of droplets of the third aqueous composition is about 20 microns to about 30 microns. In other embodiments, the preponderance of the multiplicity of droplets have an effective diameter of less than or equal to about 1, or 10, or 20, or 30, or 40, or 50, or 100, microns. Useful ranges for the effective diameter of a preponderance of the multiplicity of droplets can be selected from any value between and inclusive of about 1 micron to about 100 microns. Non-limiting examples of such ranges can include from about 1 micron to about 100 microns, from about 10 microns to about 100 microns, from about 20 microns to about 100 microns, from about 30 microns to about 100 microns, from about 40 microns to about 100 microns, from about 50 microns to about 100 microns, or from about 20 microns to about 30 microns.

As a non-limiting example, a method to disinfect a surface in need of disinfecting within a volumetric space can comprise the steps of dispersing into the volumetric space a multiplicity of droplets of a first aqueous composition consisting essentially of water, allowing a time sufficient for the first aqueous composition to distribute throughout the volumetric space, and to deposit and coalesce into a layer upon the surfaces; dispersing into the volumetric space a multiplicity of droplets of a second aqueous composition comprising a first peracid reactant compound that is selected from the group consisting of a peroxide compound and an organic acid; allowing a second time sufficient for the droplets of the second aqueous composition to deposit onto the coalesced layer of the first aqueous composition; dispersing into the volumetric space a multiplicity of droplets of a third aqueous composition comprising a second peracid reactant compound that is the other of the first peracid reactant compound; and allowing a third time sufficient for the droplets of the third aqueous composition to deposit onto the coalesced layer of the first and second aqueous composition to form a reaction layer, thereby forming a peracid in situ on the reaction layer and disinfecting the surfaces.

In another embodiment of the invention, the multiplicity of droplets of any of the aqueous compositions can be electrostatically charged. An example of electrostatic spraying is described in U.S. Pat. No. 6,692,694, the disclosure of which is incorporated by reference in its entirety. FIG. 1 illustrates an example of a commercial electrostatic spray device 10 according to the prior art. Electrostatic spray device 10 includes a housing 12; a container 14 associated with the housing 12 for storing a liquid; multiple nozzles 16 in liquid communication with the container 14 for dispensing aerosolized droplets of the liquid; and a high capacity charging system 18 capable of imparting an electrostatic charge on the droplets after they are dispersed. Those skilled in the art would appreciate that any electrostatic spray device can be utilized to disperse electrostatically-charged droplets, including devices that spray droplets having only a positive charge, devices that spray droplets having only a negative charge, and devices that are adjustable to selectively spray droplets having any desired charge. In some embodiments, an electrostatic spray device that is adjustable to selectively spray droplets having either a positive, negative, or neutral charge can be utilized.

There are several advantages that can be exploited by dispersing the droplets with an electrostatic charge, including but not limited to: a more effective and targeted dispersal onto surfaces to be disinfected, application onto non-line-of-sight vertical and under-side surfaces, and enhanced activation of the peracid reactant compounds prior to the formation of the peracid on the surface. Without being limited by theory, it is believed that applying an electrostatic charge leads to a more effective dispersal of the aqueous composition because the multiplicity of like-charged droplets repels each other according to Coulomb's law. As shown in FIG. 2, negatively charged particles 120 dispensed from the nozzle of an electrostatic spray device 116 will deposit onto all faces of a positive or neutrally-charged surface 130. Droplets will additionally distribute evenly across an area or volumetric space and deposit on to a diversity of surfaces, including the back surfaces and underside surfaces, of an object in an effort to maximize the distance from droplet to droplet.

Because of the volume of the aqueous composition dispersed in the volumetric space, the like-charged particles spontaneously coalesce into a layer on the surface. In some embodiments, the first aqueous composition is electrostatically charged to provide a uniform distribution of droplets on the surfaces to be disinfected, followed by dispersing the second aqueous composition into the volumetric space. In other embodiments, Coulomb's law can be further exploited by electrostatically charging the multiplicity of droplets of the second aqueous composition with the opposite polarity as the multiplicity of droplets of the first aqueous composition, creating an attraction between the first aqueous composition and the second aqueous composition, and ensuring that the peracid reactant compounds come into contact with each other in the coalesced layer on the surface to be disinfected.

Additionally, the electrostatic charge placed on an aqueous composition can be selected to enhance the reactivity of the peracid reactant compounds. In some embodiments, the aqueous composition that includes the peroxide compound may be electrosprayed with a negative charge, while the aqueous composition including the organic acid may be electrosprayed with a positive charge. In other embodiments, the opposite situation may occur in which the aqueous composition including the peroxide compound may be electrosprayed with a positive charge, and the aqueous composition including the organic acid may be sprayed with a negative charge. Ultimately, any combination of electrostatic charge (positive, negative, or neutral) may be applied to any aqueous composition, independent of the identity of the components present in either aqueous composition.

In addition to augmenting the deposition of the aqueous compositions on the surfaces to be disinfected and enhancing the peracid-forming reaction, utilizing electrospray brings additional supplemental benefits to the methods described herein. While the attraction that the electrostatically-charged droplets have for surfaces is beneficial for facilitating the reaction on the surfaces to be disinfected, it also provides an additional safety measure for any persons who may be in the area or volumetric space. Smaller droplets that would otherwise penetrate into someone's deep lung would instead be attracted to the surfaces of the person's nasal cavity or mouth, where their effects, if any, can be easily neutralized by the body. Additionally, the repulsion experienced by identically-charged particles can cause droplets to remain in the air for a longer period of time without being forced to the ground by gravity. Thus, larger droplet sizes can be used and disinfection of surfaces within larger volumetric spaces can be facilitated.

In another embodiment, surfaces within the volumetric space can also be grounded prior to dispersing the first aqueous composition by electrostatic spray. Because an electric attraction is created between the grounded surfaces and the charged droplets in the volumetric space, the droplets can become attracted preferentially, or only, to the grounded surfaces. As a non-limiting example, high-traffic or highly-contaminated surfaces in a hospital room such as door handles, faucets, and hospital bedrails and bars, can be targeted by grounding them prior to disinfecting, facilitating a faster turnover of the room between patients. In other embodiments, surfaces that are already ground within an area or volumetric space can be removed from the ground source prior to dispersing an electrostatically-charged first aqueous composition, in order to provide a better blanket coverage of all surfaces within the volumetric space. In further embodiments, electrostatically spraying selected grounded surfaces with the first aqueous composition can be utilized in combination with dispersing a second aqueous composition with no electrostatic charge in order to provide general surface coverage throughout the volumetric space.

Similarly, electrostatic charge can be applied to dispersed droplets of additional aqueous compositions not containing peracid reactant compounds, either to enhance the distribution of the aqueous composition throughout the volumetric space or to facilitate an attraction or repulsion between electrostatically-charged droplets dispersed in other method steps. For instance, in some embodiments, the method can comprise the steps of dispersing into the volumetric space a multiplicity of positively-charged droplets of a first aqueous composition comprising a first peracid reactant compound that is either a peroxide compound or an organic acid; allowing a time sufficient for the first aqueous composition to distribute throughout the volumetric space, and to deposit and coalesce into a layer upon the surface; dispersing into the volumetric space a multiplicity of negatively-charged droplets of a second aqueous composition comprising a second peracid reactant compound that is the other of the first peracid reactant compound; allowing a second time sufficient for the droplets of the second aqueous composition to deposit onto the coalesced layer of the first aqueous composition to form a reaction layer, thereby forming a peracid in situ on the reaction layer and disinfecting the surface; dispersing into the volumetric space positively-charged droplets of a finishing composition consisting essentially of water; and allowing a time sufficient for the third aqueous composition to distribute throughout the volumetric space. Dispersing the finishing composition with a positive charge after the dispersion and deposition of the negatively-charged second aqueous composition can facilitate the removal of any excess or lingering droplets of the second aqueous composition remaining in the volumetric space after the disinfection is complete.

In another embodiment, an electrostatic charge may be applied either prior to the aerosolization of the aqueous composition or after the composition has been dispersed. Distribution of the multiplicity of electrostatically-charged droplets can be tailored by adjusting the magnitude of the voltage applied to the nozzle on the electrostatic sprayer, nozzle size or type, and the flow rate of the aqueous composition through the nozzle.

Depending on the nature and contamination of the surfaces, the size of the volumetric space in which those surfaces are located, the compounds chosen for each of the aqueous compositions, it can be advantageous to perform the methods described herein without a person being present. Consequently, in one embodiment of the invention, a disinfecting system is provided that comprises a) housing, b) a first container for a first liquid associated with the housing; c) a second container for a second liquid associated with the housing; d) a nozzle attached to the housing, in liquid communication with at least one of the first container and the second container, for dispensing a stream of droplets of at least one of the first liquid and the second liquid; e) a means for imparting an electrostatic charge to at least the first liquid during dispensing from the nozzle; f) a microprocessor including a memory and programming, configured for dispensing a preselected amount of the first liquid and a preselected amount of the second liquid; and optionally g) a timing mechanism for controlling an amount of time between the dispensing of the first liquid, and the dispensing of the second liquid.

In another embodiment, the disinfecting system may additionally include a third container, in liquid communication with a nozzle, for a third liquid associated with the housing. In conjunction with including a third container in the disinfecting system, the microprocessor can be configured for dispensing a preselected amount of the third liquid, and the timing mechanism can control the amount of time between dispensing the first, second, and third liquids. In some embodiments, the third liquid consists essentially of water, which can be applied in any of the pre-treatment, intermediate, and finishing steps described above, either before or after dispersing either of the aqueous compositions comprising a peracid reactant compound.

Delivery of the peracid reactant compounds in aqueous compositions can be made by methods in addition to electrospraying the surfaces to be disinfected, especially where those surfaces are inside air ducts, confined spaces, or in very large volumetric spaces. In these situations, vaporizing the aqueous compositions in the ambient air or introducing them into a hot gaseous stream may be highly effective. Sterilization using these methods has been described in U.S. Pat. Nos. 8,696,986 and 9,050,384, the disclosures of which are incorporated by reference in their entireties. Similar to the other patent references described above, the methods described in these patents require that the peracid be formed and then dispensed into a volumetric space. In contrast, peracid reactant compounds are dispersed in separate application steps, thereby forming the peracid in situ only on the surfaces to be disinfected.

In another embodiment, a surface in need of disinfecting within an volumetric space containing ambient air may be disinfected using a method comprising the steps of: a) heating a first aqueous composition comprising a peroxide compound to produce a vapor comprising the peroxide compound in the ambient air; b) allowing a first time sufficient for the vapor comprising the peroxide compound to distribute throughout the volumetric space, and to cool, condense and deposit into a liquid layer upon the surface, the liquid layer comprising the peroxide compound; c) heating a second aqueous composition comprising an organic acid to produce a vapor comprising the organic acid; and d) allowing a second time sufficient for the vapor comprising the organic acid to distribute throughout the volumetric space, and to cool, condense and deposit the organic acid onto the liquid layer comprising the peroxide compound to form a reaction layer, thereby forming a peracid in situ on the reaction layer and disinfecting the surface. In further embodiments, the time sufficient for an aqueous composition dispersed as a vapor to distribute throughout the volumetric space, to cool and condense into liquid droplets, and to deposit onto the surfaces to be disinfected is at least about 10 minutes, including at least about 20 minutes, 30 minutes, 40 minutes, 50 minutes, 1 hour, or 2 hours, up to at least about 3 hours. In even further embodiments, lingering or excess vapor or droplets within the volumetric space can be exchanged using an air exchanger to facilitate the dispersion of a subsequent aqueous composition and/or to return the air within the volumetric space to habitable conditions.

In another embodiment, in order to form a vapor an aqueous composition can be pressure fed into an atomizing device wherein the composition is mechanically introduced as a high-pressure mist into ambient temperature atmospheric air, forming a mist or spray. The mist or spray is then heated and vaporized by repeatedly passing the mist or spray in close proximity to one or more heating elements integral to the atomizing device. As the aqueous composition repeatedly circulates, it further disperses into a superheated vapor containing molecular water, a peracid reactant compound, and any additional optionally-added biocides (as described above) at any user selectable temperatures, for example, above about 250° C. Alternatively, the first aqueous composition and the second composition are heated at a temperature sufficient to vaporize a mass of the first aqueous composition and of the second aqueous composition, respectively, in less than about 30 minutes, including less than about 25, or 20, or 15, or 10, or 5, minutes. In a further embodiment, the first aqueous composition and the second composition are heated at a temperature sufficient to vaporize each of the mass of the first aqueous composition and the second aqueous composition in about two minutes.

After exiting the atomizing device, the superheated vapor cools as it disperses and settles through the air. In use, the atomizing device can be located a sufficient distance from the surface to be disinfected such that the temperature of the vapor as it deposits on the surface is less than or equal to about 55° C. In some embodiments, the vapor is applied at a temperature approximating the ambient temperature in the storage facility, optimally ranging from about 10° C. to about 25° C. By allowing the vapor to cool to this temperature, the user can safely apply the vapor to both inert solid surfaces and the non-inert surfaces of agricultural products. In embodiments in which the entire method is applied over periods of time ranging from 40 minutes to 8 hours, substantially all surfaces can be disinfected within the volumetric space, killing virtually all bacteria, bacterial spores, fungi, protozoa, algae, and viruses on both stored agricultural products and on the surfaces of the storage facilities in which the agricultural products are stored.

Similar to other embodiments of this invention described above in which liquid droplets of the aqueous compositions are dispersed into the air, disinfection methods according to the present invention that involve vaporization also show a diminished effectiveness in dry environments. Thus, in some embodiments, the vaporization methods may further include the step of pre-treating the area or volumetric space by dispersing a vaporized composition consisting essentially of water to increase the humidity of the area. In other embodiments, lingering or excess vapor or droplets within the volumetric space can be exchanged using an air exchanger to facilitate the dispersion of a subsequent aqueous composition and/or to return the air within the volumetric space to habitable conditions.

In another embodiment of the invention, the first aqueous composition and the second aqueous composition can be vaporized by introducing them a hot gaseous stream prior to their dispersion into the volumetric space. In some embodiments, the heated gas stream is sterile air, although other gases such as nitrogen, $CO_2$, or inert noble gas carriers may also be employed. The gas stream may be heated to any user-controlled temperature above about 250° C. An aqueous composition may be introduced into the air stream by any means well known to one of skill in the art. In preferred embodiments, the aqueous composition is dispersed directly into the stream. Similar to the embodiments described above, once the vapor containing the aqueous composition is dispersed into the volumetric space, the time sufficient for the vapor to cool, condense, and deposit into a liquid layer upon a surface will vary depend on factors including but not limited to: the identity and concentration of the components in the aqueous composition and the nature of the material of the surface to be disinfected.

In a further embodiment of the invention, any of the above-described methods may further include the step of illuminating the surface to be disinfected with a wavelength consisting essentially of ultraviolet (UV) light. UV light is known to kill pathogens in the air, on surfaces, and in liquids. Methods employing UV light to kill pathogens are described in U.S. Pat. Nos. 6,692,694 and 8,110,538, the disclosures of which are incorporated by reference in their entireties. In addition to having its own biocidal activity, UV light can activate peroxide compounds to make them even more reactive in reactions with organic acids to form peracids. For example, hydrogen peroxide can be activated when it is bombarded by intense UV light to form two hydroxyl radicals. In preferred embodiments, once an aqueous composition including a peroxide compound has deposited and coalesced upon a surface to be disinfected, the surface is then illuminated with a wavelength consisting essentially of UV light. Alternatively, the composition containing the peroxide compound may be illuminated with a wavelength consisting essentially of UV light as it is dispersed. UV light may be generated using any means well known to one of skill in the art.

In another embodiment of the invention, the disinfectant methods described above for generating peracids on surfaces to be disinfected can be used for a variety of user-identified biocidal purposes, including antimicrobial, bleaching, or sanitizing applications. In other aspects, the generated peracids may be used to kill one or more of the food-borne pathogenic bacteria associated with a food product, including, but not limited to *Salmonella typhimurium, Campylobacter jejuni, Listeria monocytogenes*, and *Escherichia coli* 0157:H7, yeast, and mold.

In another embodiment, the peracids generated according to the methods and system of the present invention are effective for killing one or more of the pathogenic bacteria associated with a health care surfaces and instruments including but not limited to, *Salmonella typhimurium, Staphylococcus aureus, Salmonella choleraesurus, Pseudomonas aeruginosa, Escherichia coli*, Mycobacteria, yeast, and mold. In other embodiments, the generated peracids are also effective in domestic or industrial applications and can be applied in a variety of areas or volumetric spaces including but not limited passenger compartments in public transportation (FIG. 3), inside and outside surfaces of metal shipping containers (FIG. 4), operating rooms (FIG. 5), hospital patient rooms (FIG. 6), kitchens, bathrooms, factories, hospitals, dental offices, restaurants, laundry or textile services, and food processing plants.

Additionally, compositions containing peracid reactant compounds can be applied to a variety of hard or soft surfaces having smooth, irregular, or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example, paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. A variety of surfaces in a hospital patient room can be disinfected and sterilized, including walls, the floor, a bed frame, patient care equipment, bedside tables, and bedding.

Furthermore, the peracids generated according to the methods and system of the present invention are effective against a wide variety of microorganisms, such as Gram-positive organisms (*Listeria monocytogenes* or *Staphylococcus aureus*), Gram-negative organisms (*Escherichia coli* or *Pseudomonas aeruginosa*), catalase-positive organisms (*Micrococcus luteus* or *Staphylococcus epidermidis*), or sporulent organisms (*Bacillus subtilis*).

In another embodiment of the invention, the methods can be practiced using solely food-grade components. For example, though not required, the disinfectant methods in this invention can be practiced substantially free of ingredients commonly present in many commercially available surface cleaners. Examples of non-food grade components that can be omitted include, but are not limited to, aldehydes such as glutaraldehyde, chlorine- and bromine containing components, iodophore-containing components, phenolic-containing components, quaternary ammonium-containing components, and others. Furthermore, because peracids are formed in situ on the surface to be disinfected, heavy transition metals, surfactants, or other stabilizing compounds that could be used to prevent hydrolysis of the peracid prior to disinfecting the target surface are also not necessary and can be omitted from aqueous compositions coming into contact with food preparation surfaces or food itself.

Accordingly, the methods to produce peracids directly on surfaces to be disinfected can be employed on foods and plant species to reduce surface microbial populations, or at manufacturing, processing, or refrigerated and non-refrigerated transportation sites handling such foods and plant species. For example, the compositions can be used on food transport lines (e.g., as belt sprays); boot and hand wash dip-pans; food storage facilities; shipping containers; railcars; anti-spoilage air circulation systems; refrigeration and cooler equipment; beverage chillers and warmers; blanchers; cutting boards; third-sink areas; and meat chillers or scalding devices.

While particular embodiments of the invention have been described, the invention can be further modified within the spirit and scope of this disclosure. Those skilled in the art will recognize, or be able to ascertain using no more than routine experimentation, numerous equivalents to the specific procedures, embodiments, claims, and examples described herein. As such, such equivalents are considered to be within the scope of the invention, and this application is therefore intended to cover any variations, uses or adaptations of the invention using its general principles. Further, the invention is intended to cover such departures from the present disclosure as come within known or customary practice in the art to which this invention pertains and which fall within the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The contents of all references, patents, and patent applications mentioned in this specification are hereby incorporated by reference, and shall not be construed as an admission that such reference is available as prior art to the present invention. All of the incorporated publications and patent applications in this specification are indicative of the level of ordinary skill in the art to which this invention pertains, and are incorporated to the same extent as if each individual publication or patent application was specifically indicated and individually indicated by reference.

The invention is further illustrated by the following working and prophetic examples, neither of which should be construed as limiting the invention. Additionally, to the extent that section headings are used, they should not be construed as necessarily limiting. Any use of the past tense to describe an example otherwise indicated as constructive or prophetic is not intended to reflect that the constructive or prophetic example has actually been carried out.

WORKING EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. Thus, while the present invention has been described above with particularity, the following examples provide further detail in connection with what are presently deemed to be the most practical and preferred embodiments of the invention.

Example 1: Closed-System Electrospray Distribution Study

A study was conducted in accordance with embodiments of the present disclosure to evaluate the distribution of an aqueous composition containing 5% by weight acetic acid onto multiple target surfaces using an electrostatic spray device. Two analytical balances were placed inside a 1 cubic meter, transparent glove box (the “Cube”) and connected to a computer station configured to collect and record mass measurements as a function of time. Each balance had a standard reading error of 0.005 grams. On each balance, a 1000 square centimeter plastic sheet was placed inside a weighing pan. The position of each balance was staggered to be in different positions along the x, y, and z axes in relation to the electrostatic sprayer, placed at one end of the Cube.

The Cube was constructed with an external framework of wood covered on the inside with clear vinyl. The floor of the Cube was white Formica. An ante-chamber was placed on the lower portion of one of the walls of the Cube. There was an exhaust fan in the ante-chamber. Another wall of the Cube housed a door that enabled the entire wall of the Cube to be opened like a door. Makeup air when the Cube was being exhausted was provided through a portal on an upper corner on the ceiling of the Cube and adjacent to the wall opposite of the ante-chamber. The portal was covered with a HEPA filter that used a high efficiency furnace filter as a pre-filter. In order to manipulate materials inside the Cube while the Cube was closed to the outside environment, a single glove was installed on the wall opposite of the ante-chamber, and two gloves were installed adjacent to the ante-chamber itself. Shelves were installed near each glove station to enable the placement of the balances at staggered x, y, and z, positions, as described above. A digital thermometer and humidity meter were also installed inside the Cube.

The electrostatic spray device used was a Hurricane ES™ Portable Electrostatic Aerosol Applicator, which was placed inside the ante-chamber of the Cube. The makeup air for the sprayer came from the Cube and passed under the Sprayer so it could enter the back of the sprayer. This air was forced through the sprayer where it picked up the test solution and was forced through three nozzles in the path of three electrodes. The spray then passed through a short chamber containing a high intensity UV C light before passing into the Cube. The test solution feed line exited the ante-chamber and extended into a beaker seated on an analytical balance. About 24.5 grams of each test solution were passed into the Cube, giving a theoretical effective film thickness of about 3 microns. Objects to be tested were placed outside of the direct line of the sprayer so they only received an indirect spray, mimicking potential conditions of a surface to be disinfected in practice. During each experiment, all openings for the Cube were sealed from the outside environment.

The acetic acid composition was then electrostatically sprayed throughout the entire Cube for 30 seconds with a set particle size of about 15 microns. The time of application was selected to provide a 2-micron thick coating within the treatment space as measured by the balances. During the application, mass measurements from the two balances were collected and recorded by the computer. The result of the test is provided as follows:

TABLE 2

Electrospray Distribution

| | Mass - First Aqueous Composition (g) |
|---|---|
| Balance A (with 1000 $cm^2$ plate) | 0.205 +/- .005 |
| Balance B (with 1000 $cm^2$ plate) | 0.190 +/- .005 |

The mass of the first aqueous composition deposited on balance A and balance B indicated a difference of 0.015+/−0.010 grams. In combination with a qualitative observation that the inside surfaces of the Cube appeared to be equally coated with the acetic acid solution, it is believed that the electrospray method evenly distributed the first aqueous composition within the Cube.

Example 2: Preparation of First and Second Aqueous Compositions

Two separate aqueous compositions containing a peracid reactant compound, one containing acetic acid and one containing hydrogen peroxide, were prepared in accordance with embodiments of the present disclosure, which includes the following ingredients in approximate amounts.

First Aqueous Composition:
8% (w/w) Acetic Acid
15% (w/w) Ethanol
0.003% (w/w) Cinnamon Oil
76.997% (w/w) Distilled Water Second Aqueous Composition:
5% (w/w) Hydrogen Peroxide
15% (w/w) Ethanol
80% (w/w) Distilled Water The first aqueous composition and second aqueous composition were placed in separate containers until they could be dispersed on to surfaces in need of disinfecting within a volumetric space.

Example 3: Closed-System Log-Kill Studies by Sequential Addition of the Aqueous Compositions of Example 2

A study was conducted in accordance with embodiments of the present disclosure to determine the antimicrobial activity against common strains of bacteria by sequentially applying the two aqueous compositions of Example 2 to form peracids in situ directly on surfaces to be disinfected within a closed system. The closed system was the Cube used in Example 1. Cultures from commercially-available strains of four species of bacteria—*Bacillus subtilis, Micrococcus luteus, Rhodospirillum rubrum,* and *Staphylococcus epidermis*—were selected for a log-kill study because they possess several known defense mechanisms to common biocides while at the same time having different physical properties from each other. Sterilized, pre-poured agar plates were used as growth media to produce colonies of each bacteria. 8 plates were inoculated for each species. Of those 8 plates, 4 plates were exposed to the sequential application of the two aqueous compositions of Example 2, and 4 plates were held out as controls. Plates were inoculated using the standard T-method of streaking for log-kill studies, where the concentration of bacteria in the fourth quadrant of the plate is about 1,000,000× diluted with respect to the first quadrant. The test plates for each species were then placed inside the Cube with the lids open. Control plates were sealed with tape.

Upon closing the Cube, a multiplicity of droplets of the first aqueous composition was electrostatically applied to the entire Cube using a Hurricane ES™ Portable Electrostatic Aerosol Applicator. Droplets were sprayed for 30 seconds, using a flow rate of 6 oz./min, which correlates with a droplet size of 10-20 microns, according to the instructions provided by the manufacturer of the Hurricane ES™ applicator. The timing of the application of the first aqueous composition was selected to provide a coating having a calculated 2-micron thickness on the plates within the treatment space, as determined by the mass of the solution. About 1 minute after completing the spraying of the first aqueous composition, the second aqueous composition was sprayed for 3 seconds at a distance of about 6-8 inches using a hand sprayer, and the entire system was untouched for another 5 minutes. After evacuating the airspace of residual spray, the test plates were closed with their lids inside the Cube before being brought out into the ambient environment, where they were sealed with tape. During the transfer from the Cube to the outside environment, the lids of the *B. subtilis* test plates 1 and 2 were inadvertently opened. These plates were immediately closed and sealed with tape. All of the sealed test and control plates were then incubated at about 28° C. and inspected after 1, 2, and 4 days.

The results of the tests are provided as follows:

TABLE 3

| Presence of colonies after 1 day (+ or −) | | | | |
| --- | --- | --- | --- | --- |
| Plate Number | B. subtilis | M. luteus | R. rubrum | S. epidermis |
| 1 | + | − | − | − |
| 2 | + | − | − | − |
| 3 | − | − | − | − |
| 4 | − | − | − | − |

TABLE 4

| Presence of colonies after 2 days (+ or −) | | | | |
| --- | --- | --- | --- | --- |
| Plate Number | B. subtilis | M. luteus | R. rubrum | S. epidermis |
| 1 | + | − | − | − |
| 2 | + | − | − | − |
| 3 | − | − | − | − |
| 4 | − | − | − | − |

TABLE 5

| Presence of colonies after 4 days (+ or −) | | | | |
| --- | --- | --- | --- | --- |
| Plate Number | B. subtilis | M. luteus | R. rubrum | S. epidermis |
| 1 | + | − | − | − |
| 2 | + | − | − | − |
| 3 | − | − | − | − |
| 4 | − | − | − | − |

All controls produced the expected results, with positive control plates not treated with the sequentially-applied aqueous compositions containing the peracid reactant compounds showing growth for each organism characteristic of its growth within an open environment. Over the 16 control plates, there was an average of 4 colonies in the fourth quadrant of the plate, indicating that there were 4,000,000 colonies in the initial inoculation.

Colonies were observed on two *B. subtilis* test plates after 1 day. However, these test plates were the ones that were inadvertently exposed to the ambient environment after the method was completed, but before the lids were sealed. These colonies possessed a different morphology than those on the *B. subtilis* control plates. Consequently, it is believed that these colonies represent a false positive, based on bacteria that were introduced onto the plates when the lids were inadvertently opened. Because colonies were found on plates that had previously been exposed to a peracid, these results also suggest that the test plates themselves were capable of supporting bacterial growth, and that the lack of observable colonies on the rest of the test plates is a direct consequence of the disinfection method employed in the experiment. Therefore, the lack of colonies on the rest of the test plates, coupled with the approximately 4,000,000 colonies observed on the control plates, indicates that the method was effective to at least a log-6 kill rate, representing a kill of at least 99.9999% of the bacteria originally present on the plates.

Example 4: Medium-Sized Volumetric Space Electrospray Distribution Study

A study was conducted in accordance with embodiments of the present disclosure to evaluate the distribution of an aqueous composition containing 1% by weight acetic acid onto multiple target surfaces using an electrostatic spray device. The electrostatic spray device used was a Hurricane ES™ Portable Electrostatic Aerosol Applicator. The laboratory space in which the testing surfaces were located was closed off to the surrounding environment and had a volume of about 30 cubic meters, approximately the size of a small hospital room. The electrospray device was placed on a platform approximately 2-feet high and approximately 5 feet from one of the corners of the laboratory space, and was pointed to face the opposite corner, enabling testing of distribution behind the electrospray device along the y-axis (defined below). Several pH testing strips were fixed throughout the laboratory space, particularly walls, floor, ceiling, and equipment, including exposed and non-exposed surfaces. The pH strips were evaluated both prior to and after electrospraying the acetic acid composition for a change in color in response to being exposed to the acetic acid composition. Each application of the acetic acid composition was sprayed with a negative charge.

For each application, the acetic acid composition was sprayed for approximately 45 seconds using a flow rate of 6 oz/min, which correlates with a droplet size of 10-20 microns, according to the instructions provided by the manufacturer of the Hurricane ES™ applicator. After spraying finished, researchers entered the room to evaluate the pH strips. Over three trials, every pH strip exhibited a color change during each trial, indicating that the acetic acid composition contacted each strip, even pH strips that were hidden or unexposed.

The pH at each pH strip location was quantified, and the pH distribution as a function of changes in x, y, and z direction from the nozzle on the electrospray device are shown in FIG. 7. Each of the lines represent a line of best fit of data collected from each of the pH strips within the area. A lower pH value indicates that more acetic acid contacted the pH strip at that location than at a location with a higher pH value. All distances were calculated in inches. The x-axis was defined as the horizontal axis perpendicular to the outward direction of the electrospray device. The y-axis was defined as the horizontal axis parallel to the outward direction of the electrospray device. The nozzle of the electrospray device was oriented to spray at a 45° angle relative to both the x- and y-axes. The z-axis is the vertical height extending directly upward or downward from the nozzle of the sprayer. Over both the x- and z-axes, contact by the acetic acid spray generally increased as the distance from the sprayer increased, as evidenced by the decreased pH measured at those locations. However, the effect was hyperbolic and flattened out after a time. Along the y-axis however, coverage generally decreased at a further distance away from the sprayer, although approximately the same decrease was observed both in front of (positive distance values) and behind (negative distance values) the electrospray. Nonetheless, in all cases, the difference between the pH at the greatest coverage and least coverage at the measured locations was narrow, although the effect was more pronounced along the z-axis.

Example 5: Multidimensional Analysis of Reaction Parameters and their Effect on the Percent Kill of Bacteria A study was conducted in accordance with embodiments of the present disclosure to evaluate the effect of several reaction parameters on the percent kill of microbes. Reaction parameters tested include: the concentration of the peracid reactant compounds in an aqueous composition, order of addition of aqueous compositions containing peracid reactant compounds, the charge applied when dispersing peracid reactant compounds, the concentration of alcohol included in each aqueous composition, the concentration of a natural biocide or biocidal compound included in each composition, and the effect of illuminating the surface with a wavelength consisting essentially of ultraviolet light. In all experiments in which an alcohol was included in an aqueous composition, the alcohol was ethanol. In all experiments in which a natural biocide was included, the natural biocide was cinnamon oil. Typical stock solutions used in the formulation of aqueous compositions for each experiment included distilled water, 35% food-grade hydrogen peroxide, 99% glacial acetic acid, 95% ethanol, and cinnamon oil diluted to 20% concentration with ethanol.

All experiments were conducted in the Cube utilized in Example 1. The electrostatic spray device used was a Hurricane ES™ Portable Electrostatic Aerosol Applicator, modified to have the capability to disperse droplets having a negative charge, positive charge, and a neutral charge. Three different bacteria were tested in each experiment, *Bacillus subtilis, Micrococcus luteus*, and *Staphylococcus epidermidis*, according to the procedures of Example 3. The amount of bacterial kill was evaluated as a percent kill, rather than a log kill, to evaluate experiments where one or more reaction components were not included, facilitating analysis comparing results across all experiments. Petri dishes containing bacteria were graded 24 hours, 3 days, and 5 days after each experiment. Bacterial control reactions were conducted in parallel with each experiment, according to the procedures of Example 3. In order to ensure a constant humidity and to facilitate deposition of the droplets of each aqueous composition, a pre-treatment step was utilized in each experiment, where distilled water was sprayed using a neutral charge inside the Cube until the relative humidity inside the Cube registered 90% on the humidity meter.

Data for each experiment was compiled into JMP, a statistical analysis software too available from SAS Institute, Inc, which is able to analyze, model, and visualize data over several variables in order to determine correlations between variables over several dimensions. Particularly, percent kill was determined in two dimensions as a function of multiple data points collected for each reaction parameter. Using all of the compiled data, JMP software can then calculate a model that can be used to determine the effect on the percent kill of the bacteria both at untested concentrations or values for a single reaction parameter, as well as the effect of one reaction parameter on the ability of other reaction parameters within the system to affect the bacteria.

In a first set of experiments, the effect of the presence of hydrogen peroxide, acetic acid, ethanol, cinnamon oil, as well as illumination by ultraviolet light and dispersion of the aqueous compositions in the presence of an electric charge was determined. Thirteen separate reaction conditions were tested, according to Table 6, below. The value reported in the percent kill column represents the average percent kill of all three of the species of bacteria, with each experiment repeated in triplicate.

TABLE 6

| Exp # | Comments | % Kill | HP | AA | EtOH | UV | Charge | Cinn. |
|---|---|---|---|---|---|---|---|---|
| 1 | Control-No treatment | 0 | | | | | | |
| 2 | Comp 1: HP (−) ∣ Comp 2: AA (+) | 87 | x | x | | | x | |
| 3 | Comp 1: HP (−) ∣ Comp 2: AA (+) | 90 | x | x | | | x | |
| 4 | Comp 1: HP (+) ∣ Comp 2 : AA (−) | 94 | x | x | x | x | x | x |
| 5 | Comp 1: HP (−) ∣ Comp 2: AA (+) | 96 | x | x | x | x | x | x |

TABLE 6-continued

| Exp # | Comments | % Kill | HP | AA | EtOH | UV | Charge | Cinn. |
|---|---|---|---|---|---|---|---|---|
| 6 | Comp 1: AA (+) \| Comp 2: HP (−) | 95 | x | x | x | x | x | x |
| 7 | Comp 1: AA (−) \| Comp 2: HP (+) | 92 | x | x | x | x | x | x |
| 8 | Comp 1: HP/H2O \| Comp 2: none | 72 | x | | | | | |
| 9 | Comp 1: AA/H2O \| Comp 2: none | 6 | | x | | | | |
| 10 | Comp 1: EtOH/H2O \| Comp 2: none | 0 | | | x | | | |
| 11 | Comp 1: UV/H2O \| Comp 2: none | 21 | | | | x | | |
| 12 | Comp 1: H2O (−) \| Comp 2: none | 27 | | | | | x | |
| 13 | Comp 1: Cinn./H2O \| Comp 2: none | 17 | | x | | | | x |

As indicated in Table 6, "x" illustrates that the component is present in the experimental condition; "HP"=5% by weight of hydrogen peroxide; "AA"=8% by weight of acetic acid; "EtOH"=16% by weight of ethanol; "UV"=surface is illuminated by ultraviolet light during the reaction conditions; "Charge"=at least one aqueous composition is dispersed with an electrostatic charge; and "Cinn"=0.1% by weight of cinnamon oil. "Comp 1" refers to the aqueous composition dispersed first, and "Comp 2" refers to the aqueous composition dispersed second. In parentheses, the electrostatic charge of the aqueous composition as it was dispersed is shown, where applicable. In experiments in which ethanol was present in the reaction conditions, ethanol was included in both aqueous compositions. In experiments in which cinnamon oil was present in the reaction conditions, cinnamon oil was added in the composition along with acetic acid. In experiments in which the surface was exposed to UV light, the procedures according to Example 1 were utilized. Experiments 2 through 7 represent reaction conditions in which a peracid reactant compound was included in each of the dispersed aqueous compositions, while Experiments 8 through 13 represent control reactions in which one or both of the peracid reactant compounds was omitted.

The results in Table 6 illustrate that in experiments in which both peracid reactant compounds are included (Experiments 2 through 7), the percent kill is demonstrably larger than in any of the Experiments 8 through 13 in which one or zero peracid reactant compounds is included. Furthermore, the percent kill of Experiments 8 and 9 together, where either hydrogen peroxide or acetic acid only are included, are noticeably less than in any of Experiments 2 through 7 where both compounds are included. This result demonstrates that a peracid is being formed on the surface and that the increased bacterial kill is a result of forming the peracid. Experiments 4 through 7, which alter the order of dispersion and charge associated with each aqueous composition, each illustrate similar percent kill results to each other. The reaction conditions in Experiments 4 through 7, particularly 4 through 6, do illustrate that at least one of the ethanol, UV, or cinnamon oil are having an increased effect on the percent kill relative to reactions in which those components are absent (Experiments 2 and 3).

In a second set of experiments, the effects of concentration of the peracid reactant compounds, ethanol, and cinnamon oil were studied as a function of the order of addition and electrostatic charge over the course of 174 separate experiments. In several reactions, the concentration of some reaction components was kept intentionally low in order to determine the effect of other reaction conditions. The tested concentrations of acetic acid ranged from 0 to 15% by weight of the aqueous composition; the tested concentrations of hydrogen peroxide ranged from 0 to 10% by weight of the aqueous composition; the tested concentrations of ethanol ranged from 0 to 16% by weight of the aqueous composition; and the tested concentrations of cinnamon oil ranged from 0% to 0.16% by weight of the aqueous composition.

Percent kill data from each experiment as a function of altering one or more of the reaction variables were compiled into the JMP program. Data from all 174 experiments were utilized to calculate a model for predicting the average kill over all reaction conditions and tested concentration ranges for each reaction component. The calculated model determined that there were nine statistically significant ($R^2$=97%) independent variables that had an effect on the percent kill, including: the acetic acid concentration, the polarity of the charge of the second dispersed aqueous composition, cinnamon oil concentration, the presence and order of addition of the composition comprising hydrogen peroxide, hydrogen peroxide concentration, and whether the surface was illuminated with ultraviolet light. Additional terms, including the square of the order of addition of the composition comprising hydrogen peroxide, the square of the hydrogen peroxide concentration, and whether the surface was illuminated with ultraviolet light in conjunction with the addition of hydrogen peroxide, where also statistically relevant.

Figure 8:
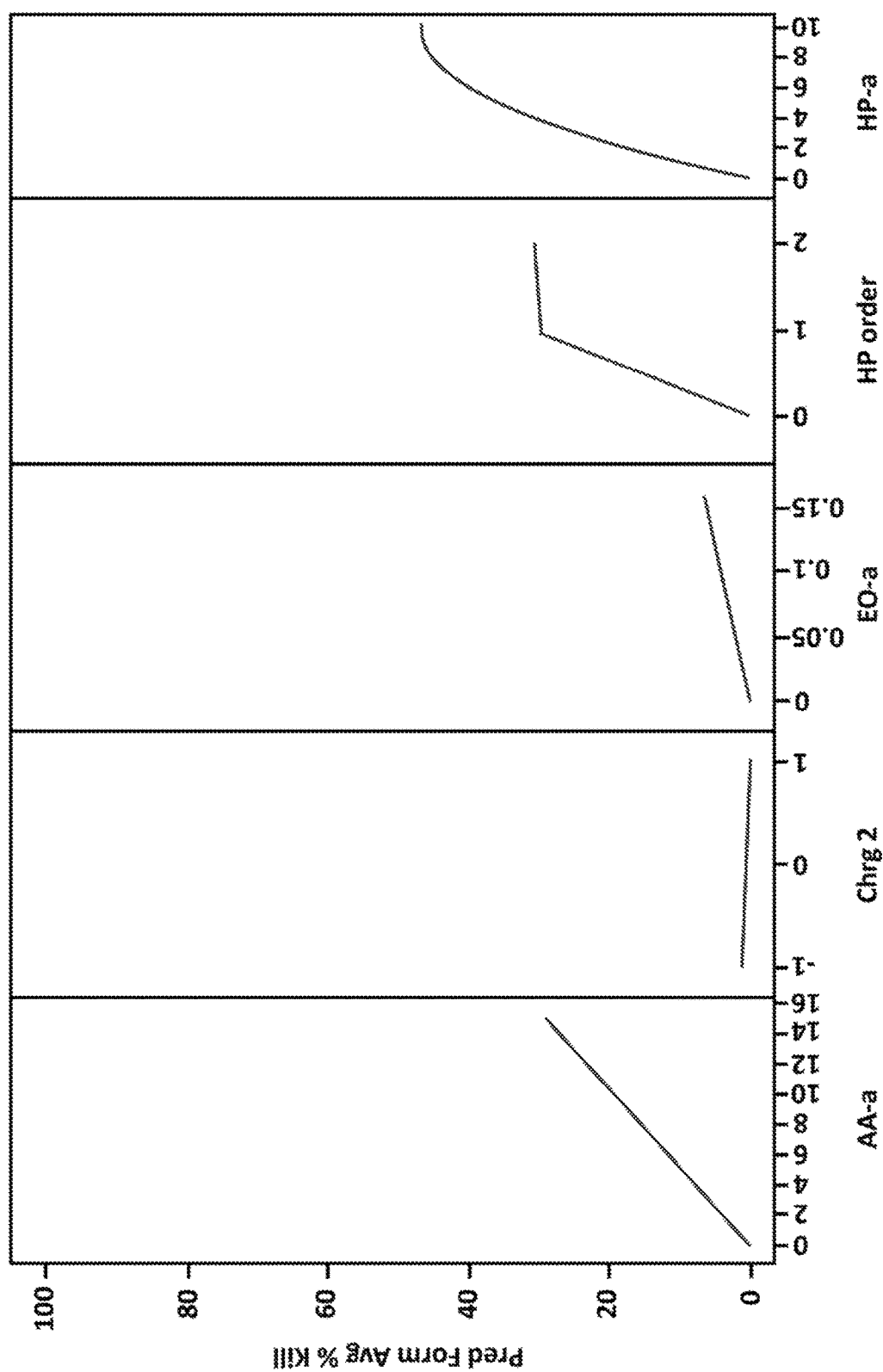
FIG. 8 shows plots illustrating the independent effect of several experimental variables on the percent kill of bacteria.
Figure 9:
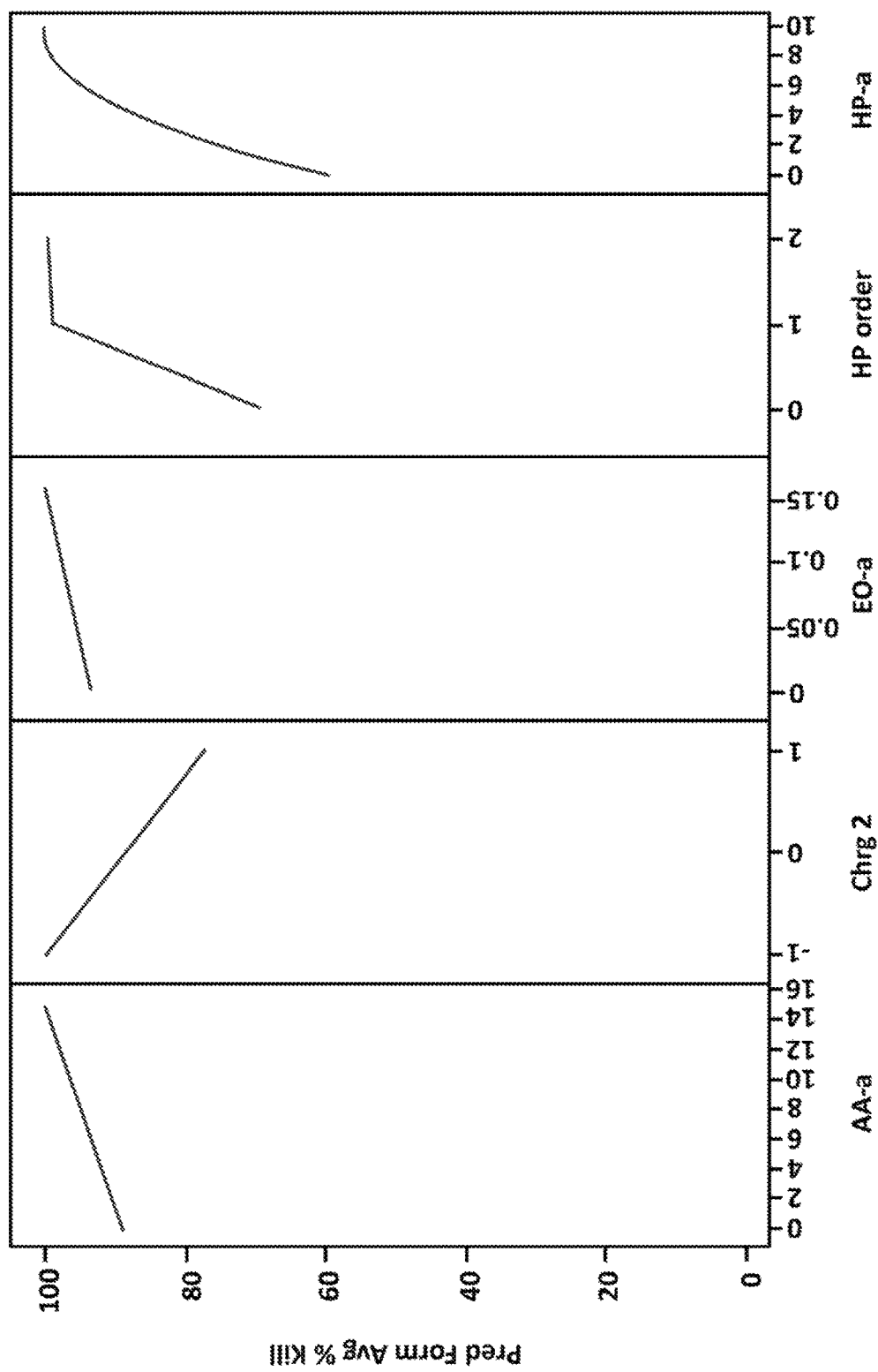
FIG. 9 shows plots illustrating the correlative effect of several experimental variables on the percent kill of bacteria.

FIGS. 4 and 5 illustrate the effects on the percent kill of each of the components considered separately (FIG. 8) and when analyzed together (FIG. 9). In FIG. 8, when the actual concentrations of acetic acid (AA-a), cinnamon oil (EO-a), and hydrogen peroxide (HP-a) are all 0, the model predicts that the percent kill of the bacteria is 0. This result is equivalent to control reactions in which none of the reaction components are added. Although the plot for charge of the second composition (Chrg 2) and order of addition (HP order) illustrate continuous lines, these plots are artifacts of the JMP program. For the charge of the second composition, a value of −1 indicates a negative charge, a value of 0 indicates a neutral charge, and a value of +1 indicates a positive charge. For the order of addition, an HP order value of 0 indicates that hydrogen peroxide is not present, an HP order value of 1 indicates that hydrogen peroxide was dispersed in the first aqueous composition, and an HP order value of 2 indicates that hydrogen peroxide was dispersed in the second aqueous composition. Not surprisingly, the addition of hydrogen peroxide has a more noticeable effect on the percent kill than does adding an equivalent amount of acetic acid. However, the effect of adding HP appears to level off at higher concentrations, whereas the correlation of adding more acetic acid appears to be linear. This phenomenon may indicate that acetic acid must be present at a concentration higher than that tested in these experiments in order to maximize the effect of hydrogen peroxide and cause the relationship between hydrogen peroxide concentration and percent kill to be more linear, if such a relationship exists. On the other hand, the leveling off at higher concentrations of hydrogen peroxide may indicate a quenching effect on the percent kill of the bacteria.

On the other hand, FIG. 9 illustrates the maximum effect that each reaction parameter has on the percent kill. In each case, where the plot for a particular reaction parameter reaches 100%, it indicates the optimum value for each variable, over all concentrations and reaction conditions tested. The value above each x-axis label indicates the optimum value for each variable. Interestingly, the optimum value for acetic acid and cinnamon oil concentrations sit at the maximum tested value (15% by weight of acetic acid, 0.16% by weight of cinnamon oil), indicating that higher concentrations of acetic acid and cinnamon oil can likely be used to have an even greater effect on killing bacteria. Surprisingly, while the plots of each of the variables generally have the same profile as in FIG. 8, the plot for the charge on the second aqueous composition illustrates a strong preference for being dispersed with a negative charge. This is true even though the percent kill is nearly identical whether the aqueous composition comprising hydrogen peroxide is dispersed first or second. Consequently, the abundance of electrons associated with dispersing the second aqueous composition with a negative charge appears to enhance the reactivity of the peracid as it is formed.

In a final set of experiments, given the statistically significant presence of cinnamon oil on the percent kill of bacteria, the concentration effects of cinnamon oil, as well as the effect of other natural biocides, was tested, using a similar procedure as above. The natural biocide was dispersed as part of the first aqueous composition along with acetic acid, and hydrogen peroxide was dispersed in the second aqueous composition. 16% by weight isopropyl alcohol (i-PrOH) was present in both aqueous compositions. Four different concentrations of cinnamon oil were tested: 0.065% by weight; 0.13% by weight; 0.20% by weight; and 0.26% by weight. Additionally, thyme oil (Thym), clove oil (Cloy), and methylglyoxal (MGly) were also tested at 0.026% by weight in separate experiments. One experiment was conducted in which each of the four natural biocides were included in the first aqueous composition at a concentration of 0.065% by weight. Where present, hydrogen peroxide and acetic acid were typically added at 10% by weight, although in three of the experiments, they comprised only 5% by weight of their respective aqueous compositions. The reaction parameters and results are presented below in Table 7.

TABLE 7

| Exp. # | HP % (w/w) | AA % (w/w) | Cinn % (w/w) | Thym % (w/w) | Clov % (w/w) | Mgly % (w/w) | % Kill |
|---|---|---|---|---|---|---|---|
| 1 | 10 | 10 | 0 | 0 | 0 | 0 | 81.0 |
| 2 | 0 | 0 | 0.26 | 0 | 0 | 0 | 44.0 |
| 3 | 10 | 10 | 0.26 | 0 | 0 | 0 | 88.2 |
| 4 | 10 | 10 | 0 | 0.26 | 0 | 0 | 99.4 |
| 5 | 10 | 10 | 0 | 0 | 0.26 | 0 | 97.3 |
| 6 | 10 | 10 | 0 | 0 | 0 | 0.26 | 98.8 |
| 7 | 10 | 10 | 0.065 | 0.065 | 0.065 | 0.065 | 99.4 |
| 8 | 10 | 10 | 0.13 | 0 | 0 | 0 | 99.4 |
| 9 | 10 | 10 | 0.2 | 0 | 0 | 0 | 93.4 |
| 10 | 10 | 0 | 0 | 0 | 0 | 0 | 79.4 |
| 11 | 0 | 0 | 0.26 | 0 | 0 | 0 | 44.0 |
| 12 | 10 | 0 | 0.26 | 0 | 0 | 0 | 73.7 |
| 13 | 10 | 10 | 0.26 | 0 | 0 | 0 | 88.2 |
| 14 | 5 | 5 | 0.26 | 0 | 0 | 0 | 67.9 |
| 15 | 5 | 5 | 0 | 0 | 0 | 0 | 60.1 |
| 16 | 10 | 0 | 0.13 | 0 | 0 | 0 | 81.5 |
| 17 | 10 | 0 | 0.2 | 0 | 0 | 0 | 68.4 |
| 18 | 5 | 5 | 0.13 | 0 | 0 | 0 | 71.0 |

As illustrated in Table 7, reactions containing 10% by weight of hydrogen peroxide and acetic acid along with the highest concentrations of natural biocides had the strongest effect on the percent kill. Looking at Experiments 3 through 6, cinnamon oil was the weakest of the four natural biocides tested at 0.26% by weight, as thyme oil, clove oil, and methylglyoxal at the same concentration were all more effective than cinnamon oil. However, Experiment 8, in which cinnamon oil was present at only 0.13% by weight, was more effective than when cinnamon oil was included at 0.26% percent by weight, indicating a possible quenching issue at higher concentrations of cinnamon oil that are not exhibited by the other natural biocides. Nonetheless, the high effectiveness of compositions containing a natural biocide illustrates the effectiveness of including such compounds in at least one of the aqueous compositions according to methods of the present invention.

We claim:

1. A method for disinfecting a surface in need of disinfecting within a volumetric space, comprising the steps of:
   (a) dispersing into the volumetric space a multiplicity of droplets of a first aqueous composition comprising a first peracid reactant compound that is either a peroxide compound or an organic acid compound, wherein the multiplicity of droplets of the first aqueous composition deposits and coalesces into a first aqueous composition layer upon the surface; and
   (b) dispersing into the volumetric space a multiplicity of droplets of a second aqueous composition comprising a second peracid reactant compound that is the other of the first peracid reactant compound, wherein the multiplicity of droplets of the second aqueous composition deposits onto the coalesced first aqueous composition layer to form a reaction layer upon the surface, thereby forming a peracid in situ within the reaction layer and disinfecting the surface.

2. The method of claim 1, wherein a preponderance of the multiplicity of droplets of the first aqueous composition and a preponderance of the multiplicity of droplets of the second aqueous composition have an effective diameter of at least 1 micron, and up to about 100 microns.

3. The method of claim 2, wherein a preponderance of the multiplicity of droplets of the first aqueous composition and a preponderance of the multiplicity of droplets of the second aqueous composition have an effective diameter between about 10 microns and about 25 microns.

4. The method of claim 1, wherein the method further comprises the step of allowing a first time sufficient for the multiplicity of droplets of the first aqueous composition to distribute throughout the volumetric space prior to depositing and coalescing into a layer upon the surface, wherein the first time sufficient for the multiplicity of droplets of the first aqueous composition to distribute throughout the volumetric space is at least 30 seconds, and up to at least 30 minutes.

5. The method of claim 4, wherein the method further comprises the step of allowing a second time sufficient for the multiplicity of droplets of the second aqueous composition to distribute throughout the volumetric space prior to depositing onto the coalesced first aqueous composition layer and forming a reaction layer upon the surface, wherein the second time sufficient for the multiplicity of droplets of the second aqueous composition to distribute throughout the volumetric space is at least 30 seconds, and up to at least 30 minutes.

6. The method of claim 1, wherein an amount of the dispersed first aqueous composition and an amount of the dispersed second aqueous composition are sufficient to provide the reaction layer with a substantially uniform thickness of at least about 1 micron, and up to about 20 microns.

7. The method of claim 1, wherein the aqueous composition comprising the peroxide compound comprises between about 0.1% and about 25% by weight of hydrogen peroxide.

8. The method of claim 7, wherein the aqueous composition comprising the organic acid comprises between about 0.5% and about 50% by weight of a carboxylic acid selected from the group consisting of formic acid, acetic acid, citric acid, succinic acid, oxalic acid, propanoic acid, lactic acid, butanoic acid, pentanoic acid, and octanoic acid.

9. The method of claim 8, wherein the organic acid is acetic acid.

10. The method of claim 1, wherein the first peracid reactant compound is an organic acid and the second peracid reactant compound is a peroxide compound.

11. The method of claim 1, wherein at least one of the first aqueous composition and the second aqueous composition further comprises one or more alcohols, wherein the total weight of the one or more alcohols relative to the weight of the respective aqueous composition is between about 0.05% and about 70% by weight.

12. The method of claim 11, wherein the one or more alcohols comprise up to about 15% by weight of the aqueous composition, and include at least one lower-chain alcohol selected from the group consisting of ethanol, isopropanol, and t-butanol.

13. The method of claim 1, wherein the multiplicity of droplets of at least one of the first aqueous composition and the second aqueous composition are dispersed into the volumetric space as electrostatically-charged droplets.

14. The method of claim 13, wherein the multiplicity of droplets of the first aqueous composition and the multiplicity of droplets of the second aqueous composition are dispersed into the volumetric space as electrostatically-charged droplets, wherein the electrostatically-charged droplets of the second aqueous composition have the opposite charge polarity as the electrostatically-charged droplets of the first aqueous composition.

15. The method of claim 14, wherein the first aqueous composition comprises an organic acid and the multiplicity of droplets of the first aqueous composition is positively charged, and the multiplicity of droplets of the second aqueous composition is negatively charged.

16. The method of claim 1, wherein at least about 99.0% by weight of the components of the first aqueous composition and the second aqueous composition comprise compounds having a standard vapor pressure of at least about 1.0 mm Hg at 20° C.

17. The method of claim 1, wherein the method further comprises the step of dispersing into the volumetric space, after dispersing the second aqueous composition, a multiplicity of droplets of a third aqueous composition consisting essentially of water.

18. The method of claim 1, wherein the method further comprises the step of dispersing into the volumetric space a multiplicity of droplets of a third aqueous composition consisting essentially of water, prior to dispersing the first aqueous composition into the volumetric space.

19. The method of claim 18, wherein an amount of the third aqueous composition is dispersed into the volumetric space to raise the relative humidity inside the volumetric space to at least about 60 percent, up to about 95 percent.

20. The method of claim 1, wherein at least one of the first aqueous composition or the second aqueous composition further comprises one or more natural biocides, wherein the total weight of the one or more natural biocides relative to the weight of the aqueous composition is between 0.001% to about 1% by weight, and wherein the one or more biocides are selected from the group consisting of manuka honey and the essential oils of oregano, thyme, lemongrass, lemons, oranges, anise, cloves, aniseed, cinnamon, geraniums, roses, mint, peppermint, lavender, citronella, eucalyptus, sandalwood, cedar, rosmarin, pine, vervain fleagrass, and ratanhiae, and combinations thereof.

21. The method of claim 1, wherein at least one of the first aqueous composition or the second aqueous composition further comprises one or more natural biocidal compounds, wherein the total weight of the one or more natural biocidal compounds relative to the weight of the aqueous composition is between 0.001% to about 1% by weight, and wherein the one or more natural biocidal compounds are selected from the group consisting of methylglyoxal, carvacrol, eugenol, linalool, thymol, p-cymene, myrcene, borneol, camphor, caryophillin, cinnamaldehyde, geraniol, nerol, citronellol, and menthol.

22. The method of claim 17, wherein the multiplicity of droplets of the third aqueous composition is dispersed into the volumetric space as electrostatically-charged droplets.

* * * * *